US007078510B2

(12) United States Patent
Robbins

(10) Patent No.: US 7,078,510 B2
(45) Date of Patent: Jul. 18, 2006

(54) ROBUST, INDUCIBLE CARDIAC PREFERRED EXPRESSION SYSTEM FOR TRANSGENESIS

(75) Inventor: Jeffrey Robbins, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 160 days.

(21) Appl. No.: 10/613,728

(22) Filed: Jul. 3, 2003

(65) Prior Publication Data

US 2004/0010813 A1    Jan. 15, 2004

Related U.S. Application Data

(60) Provisional application No. 60/393,525, filed on Jul. 3, 2002.

(51) Int. Cl.
C07H 21/04    (2006.01)
C12N 5/00    (2006.01)
C12N 15/74    (2006.01)

(52) U.S. Cl. .................. 536/23.1; 435/320.1; 435/325
(58) Field of Classification Search ..................... None
See application file for complete search history.

(56) References Cited

U.S. PATENT DOCUMENTS 6,353,151 B1    3/2002 Leinwand et al.

FOREIGN PATENT DOCUMENTS

WO    WO 00/78119 A    12/2000

OTHER PUBLICATIONS

Rindt H, An in vivo analysis of transcriptional elements in the mouse alpha myosin heavy chain gene promoter, 1995, Transgenic Res. vol. 4, pp. 397-405.*
Verma IM, Gene Therapy: Twenty-first century medicine, 2005, Annu. Rev. Biochem. vol. 74, pp. 711-738.*
Parekh-Olmedo H, Gene therapy progress and prospects: targeted gene repair, 2005, Gene Therapy, vol. 12, pp. 639-646.*
Concalves M, A concise peer into the background, initial thoughts, and practices of human gene therapy, 2005, BioEssays, vol. 27, pp. 506-517.*
Robbins et al., Mouse Embryonic Stem Cells Express the Cardiac Myosin Heavy Chain Genes during Development in Vitro, The Journal of Biological Chemistry, vol. 265, No. 20, Jul. 15, 1990 Issue, pp. 11905-11909, The American Society for Biochemistry and Molecular Biology, Inc., U.S.A., copyright 1990.
Subramaniam et al., Tissue-specific Regulation of the a-Myosin Heavy Chain Gene Promoter in Transgenic Mice, The Journal of Biological Chemistry, vol. 266, No. 36, Dec. 25, 1991 Issue, pp. 24613-24620, The American Society for Biochemistry and Molecular Biology, Inc., U.S.A., copyright 1991.
Subramaniam et al., Transgenic Analysis of the Thyroid-responsive Elements in the a-Cardiac Myosin Heavy Chain Gene Promoter, The Journal of Biological Chemistry, vol. 268, No. 6, Feb. 25, 1993 Issue, pp. 4331-4336, The American Society for Biochemistry and Molecular Biology, Inc., U.S.A., copyright 1993.
Dorn II et al., Myosin heavy chain regulation and myocyte contractile depression after LV hypertrophy in aortic-banded mice, Special Communication, vol. 0363-6135/94, pp. H400-H405, The American Physiological Society, copyright 1994.
Palermo et al., Transgenic Remodeling of the Contractile Apparatus in the Mammalian Heart, Circulation Research, 1996: 78:504-509, American Heart Assoc., U.S.A., c 1996.
Sanbe et al, Abnormal Cardiac Structure and Function in Mice Expressing Nonphosphorylatable Cardiac Regulatory Myosin Light Chain 2, The Journal of Biological Chemistry, vol. 274, No. 30, Jul. 23, 1990 Issue, pp. 21085-21094, The American Society for Biochemistry and Molecular Biology, Inc., U.S.A., copyright 1999.
Sanbe et al., Examining the in Vivo Role of the Amino Terminus of the Essential Myosin Light Chain, The Journal of Biological Chemistry, vol. 276, No. 35, Aug. 31, 2001 Issue, pp. 32682-32686, The American Society for Biochemistry and Molecular Biology, Inc., U.S.A., copyright 2001.
James et al., Transgenic Rabbits Expressing Mutant Essential Light Chain do not Develop Hypertrophic Cardiomyopathy, J Mol Cell Cardiol 00.1-10 (2002), Elsevier Science Ltd., U.S.A., copyright 2002.
Sanbe et al., Reengineering Inducible Cardiac-Specific Transgenesis With an Attenuated Myosin Heavy Chain Promoter, Circulation Research, 2003;92:609) American Heart Association, U.S.A., copyright 2003.

(Continued)

Primary Examiner—Ram R. Shukla
Assistant Examiner—David A. Montanari
(74) Attorney, Agent, or Firm—Taft, Stettinius & Hollister, LLP

(57) ABSTRACT

The methods and compositions of the present invention find use in altering cardiac-preferred expression in transgenic animals. The compositions of the invention include isolated nucleic acid molecules, expression cassettes, animal cells, transgenic animals, and transgenic mice. The transgenic animals of the invention exhibit inducible cardiac preferred expression of a nucleotide sequence of interest. The methods allow generation of transgenic animals with altered cardiac preferred expression of the nucleotide sequence of interest. In particular, the invention provides a method for altering the susceptibility of a transgenic animal to cardiopathy. A transgenic animal of the invention finds use in identifying anti-cardiopathic compounds.

8 Claims, 3 Drawing Sheets

OTHER PUBLICATIONS

Rahkonen et al, "Characterization of the murine TIMP4 gene, localization within intron 5 of the synapsin 2 gene and tissue distribution of the mRNA," Biochimica et Biophysica Acta, Aug. 19, 2002, p. 45-abstract, vol. 1577(1).

Charron et al. "Cooperative Interaction between GATA-4 and GATA-6 Regulates Myocardial Gene Expression," Molecular and Cellular Biology, Jun. 1999, p. 4355-4365, vol. 19-6.

Dellow et al. "Identification of novel, cardiac-restricted transcription factors binding to a CACC-box within the human cardiac troponin I promoter," Cardiovascular Research, Apr. 2001, p. 24-abstract, vol. 50-1.

Grepin et al. "A Hormone-Encoding Gene Identifies a Pathway for Cardiac but Not Skeletal Muscle Gene Transcription," Molecular and Cellular Biology, May 1994, p. 3115-3129, vol. 14-5.

Kiewitz et al. "Transcriptional Regulation of S100A1 and expression during mouse heart development," Biochimica et Biophysica Acta, Dec. 20, 2000, p. 207-abstract, vol. 1498-2/3.

Majalahti-Palviainen et al. "Gene Structure of a New Cardiac Peptide Hormone: A Model for Heart-Specific Gene Expression," Endocrinology, 2000, p. 731-740, vol. 141-2.

* cited by examiner

SEQUENCE LISTING

```
<160> NUMBER OF SEQ ID NOS: 10

<210> SEQ ID NO 1
<211> LENGTH: 5735
<212> TYPE: DNA
<213> ORGANISM: Artificial Sequence
<220> FEATURE:
<223> OTHER INFORMATION: Inducible Cardiac preferred promoter

<400> SEQUENCE: 1
ggatcctgca aggtcacaca agggtctcca cccaccaggt gccctagtct caatttcagt      60
ttccatgcct tgttctcaca atgctggcct ccccagagct aatttggact ttgttttat     120
```

-continued

| | |
|---|---|
| ttcaaaaggg cctgaatgag gagtagatct tgtgctaccc agctctaagg gtgcccgtga | 180 |
| agccctcaga cctggagcct ttgcaacagc cctttaggtg aaagcagaat aaagcaattt | 240 |
| tccttaaagc caaaatcctg cctctagact cttcttctct gacctcggtc cctgggctct | 300 |
| agggtgggga ggtggggctt ggaagaagaa ggtggggaag tggcaaaagc cgatccctag | 360 |
| ggccctgtga agttcggagc cttccctgta cagcactggc tcatagatcc tcctccagcc | 420 |
| aaacatagca agaagtgata cctcctttgt gacttcccca ggcccagtac ctgtcaggtt | 480 |
| gaaacaggat ttagagaagc ctctgaactc acctgaactc tgaagctcat ccaccaagca | 540 |
| agcacctagg tgccactgct agttagtatc ctacgctgat aatatgcaga gctgggccac | 600 |
| agaagtcctg gggtgtagga actgaccagt gacttttcag tcggcaaagg tatgaccccc | 660 |
| tcagcagatg tagtaatgtc cccttagatc ccatcccagg caggtctcta agaggacatg | 720 |
| ggatgagaga tgtagtcatg tggcattcca aacacagcta tccacagtgt cccttgcccc | 780 |
| ttccacttag ccaggaggac agtaaccttg gcctatcttt cttcctcccc atcctcccag | 840 |
| gacacacccc ctggtctgca gtattcattt cttccttcac gtcccctctg tgacttccat | 900 |
| ttgcaaggct tttgacctct gcagctgctg aagatagag tttggccctg ggtgtggcaa | 960 |
| gccatctcaa gagaaagcag acaacagggg gaccagattt tggaaggatc aggaactaaa | 1020 |
| tcactggcgg gcctggggt agaaaaaaga gtgagtgagt ccgctccagc taagccaagc | 1080 |
| tagtccccga gatactctgc cacagctggg ctgctcgggg tagctttagg aatgtgggtc | 1140 |
| tgaaagacaa tgggattgga agacatctct ttgagtctcc cctcaacccc acctacagac | 1200 |
| acactcgtgt gtggccagac tcctgttcaa cagccctctg tgttctgacc actgagctag | 1260 |
| gcaaccagag catgggccct gtgctgagga tgaagagttg gttaccaata gcaaaaacag | 1320 |
| caggggaggg agaacagaga acgaaataag gaaggaagaa ggaaaggcca gtcaatcaga | 1380 |
| tgcagtcaga agagatggga agccaacaca cagcttgagc agaggaaaca gaaaagggag | 1440 |
| agattctggg cataaggagg ccacagaaag aagagcccag gccccccaag tctcctcttt | 1500 |
| ataccctcat cccgtctccc aattaagccc actcttcttc ctagatcaga cctgagctgc | 1560 |
| agcgaagaga cccgtaggga ggatcacact ggatgaagga gatgtgtgga gaagtccagg | 1620 |
| gcaacctaag agccagagcc taaaagagca agagataaag gtgcttcaaa ggtggccagg | 1680 |
| ctgtgcacac agagggtcga ggactggtgg tagagcctca agataaggat gatgctcaga | 1740 |
| atgggcgggg ggggggattc tgggggggg agagagaagg tgagaaggag cctggaacag | 1800 |
| agaatctgga agcgctggaa acgataccat aaagggaaga acccaggcta cctttagatg | 1860 |
| taaatcatga aagacaggga gaagggaagc tggagagagt agaaggaccc cggggcaaga | 1920 |
| catggaagca aggacaagcc aggttgagcg ctccgtgaaa tcagcctgct gaaggcagag | 1980 |
| ccctggtatg agcaccagaa cagcagaggc tagggttaat gtcgagacag ggaacagaag | 2040 |
| gtagacacag gaacagacag agacggggga gccaggtaac aaaggaatgg tccttctcac | 2100 |
| ctgtggccag agcgtccatc tgtgtccaca tactctagaa tgttcatcag actgcagggc | 2160 |
| tggcttggga ggcagctgga aagagtatgt gagagccagg ggagacaagg gggcctagga | 2220 |
| aaggaagaag agggcaaacc aggccacaca agagggcaga gcccagaact gagttaactc | 2280 |
| cttccttgtt gcatcttcca taggaggcag tgggaactct gtgaccacca tcccccatga | 2340 |
| gcccccacta cccataccaa gtttggcctg agtggcattc taggttccct gaggacagag | 2400 |
| cctggccttt gtctcttgga cctgacccaa gctgacccaa tgttctcagt acctttgaat | 2460 |
| gccctcaaga gcttgagaac caggcagtga catattaggc catgggctaa ccctggagct | 2520 |

-continued

```
tgcacacagg agcctcaagt gacctccagg gacacagctg cagacaggtg gcctttatcc    2580
ccaaagagca accatttggc ataggtggct gcaaatggga atgcaaggtt gaatcaggtc    2640
ccttcaagaa tactgcatgc aagacctaag accoctggag agaggggtat gctcctgccc    2700
ccacccacca taaggggagt gaactatcct agggggctgg cgaccttggg gagacaccac    2760
attactgaga gtgctgagcc cagaaaaact gaccgccctg tgtcctgccc acctccacac    2820
tctagagcta tattgagagg tgacagtaga tagggtggga gctggtagca gggagagtgt    2880
tcctgggtgt gagggtgtag gggaaagcca gagcagggga gtctggcttt gtctcctgaa    2940
cacaatgtct acttagttat aacaggcatg acctgctaaa gacccaacat ctacgacctc    3000
tgaaaagaca gcagccctgg aggacagggg ttgtctctga gccttgggtg cttgatggtg    3060
ccacaaagga gggcatgagt gtgagtataa ggccccagga gcgttagaga agggcacttg    3120 ggaagggggtc agtctgcaga gcccctatcc atggaatctg gagcctgggg ccaactggtg    3180
taaatctctg ggcctgccag gcattcaaag cagcacctgc atcctctggc agcctgggga    3240
ggcggaaggg agcaaccccc cacttatacc ctttctccct cagccccagg attaacacct    3300
ctggccttcc cccttcccac ctcccatcag gagtggaggg ttgcagaggg agggtaaaaa    3360
cctacatgtc caaacatcat ggtgcacgat atatggatca gtatgtgtag aggcaagaaa    3420
ggaaatctgc aggcttaact gggttaatgt gtaaagtctg tgtgcatgtg tgtgtgtctg    3480
actgaaaacg ggcatggctg tgcagctgtt cagttctgtg cgtgaggtta ccagactgca    3540
ggtttgtgtg taaattgccc aaggcaaagt gggtgaatcc cttccatggt ttaaagagat    3600
tggatgatgg cctgcatctc aaggaccatg gaaaatagaa tggacactct atatgtgtct    3660
ctaagctaag gtagcaaggt cttttggagga cacctgtcta gagatgtggg caacagagac    3720
tacagacagt atctgtacag agtaaggaga gagaggaggg ggtgtagaat tctcttacta    3780
tcaaagggaa actgagtcgt gcacctgcaa agtggatgct ctccctagac atcatgactt    3840
tgtctctggg gagccagcac tgtggaactt caggtctgag agagtaggag gctcccctca    3900
gcctgaagct atgcagatag ccaggggttga aaggggggaag ggagagcctg ggatgggagc    3960
ttgtgtgttg gaggcagggg acagatatta agcctggaag agaaggtgac ccttacccag    4020
ttgttcaact caccccttcag attaaaaata actgaggtaa gggcctgggt aggggaggtg    4080
gtgtgagacg ctcctgtctc tcctctgcat gccctgaggc cctttgggga ggaggaatgt    4140
gcccaaggac taaaaaaagg ccatggagcc agaggggcga gggcaacaga cctttcatgg    4200
gcaaaccttg gggcccgtag tgatcgattg acaagaactc gccaatcgat acccttcttc    4260
ttctaacgga caggagggaa ctcgagttta ccactcccta tcagtgatag agaaaagtga    4320
aagtcgagtt taccactccc tatcagtgat agagaaaagt gaaagtcgag tttaccactc    4380
cctatcagtg atagagaaaa gtgaaagtcg agtttaccac tccctatcag tgatagagaa    4440
aagtgaaagt cgagtttacc actccctatc agtgatagag aaaagtgaaa gtcgagttta    4500
ccactcccta tcagtgatag agaaaagtga agtcgagtt taccactccc tatcagtgat    4560
agagaaaagt gaaagtcgag ctcggtacca gcagaggact ccaaatttag gcagcaggca    4620
tatgggatgg gatataaagg ggctggagca ctgagagctg tcagagattt ctccaaccca    4680
ggtaagaggg agtttcgggt gggggctctt cacccacacc agacctctcc ccacctagaa    4740
ggaaactgcc tttcctggaa gtggggttca ggccggtcag agatctgaca gggtggcctt    4800
ccaccagcct gggaagttct cagtggcagg aggtttccac aagaaacact ggatgcccct    4860
```

```
tcccttacgc tgtcttctcc atcttcctcc tggggatgct cctccccgtc ttggtttatc    4920
ttggctcttc gtcttcagca agatttgccc tgtgctgtcc actccatctt tctctactgt    4980
ctccgtgcct tgccttgcct tcttgcgtgt ccttcctttc cacccatttc tcacttcacc    5040
ttttctcccc ttctcatttg tattcatcct tccttccttc cttccttcct tccttccttc    5100
cttccttcct tcctttctcc cttccttcct tccttccttc cttccttcct tccttccttc    5160
ctgtgtcaga gtgctgagaa tcacacctgg ggttcccacc cttatgtaaa caatcttcca    5220
gtgagccaca gcttcagtgc tgctgggtgc tctcttacct tcctcacccc ctggcttgtc    5280
ctgttccatc ctggtcagga tctctagatt ggtctcccag cctctgctac tcctcttcct    5340
gcctgttcct ctctctgtcc agctgcgcca ctgtggtgcc tcgttccagc tgtggtccac    5400
attcttcagg attctctgaa aagttaacca ggtgagaatg tttcccctgt agacagcaga    5460
tcacgattct cccggaagtc aggcttccag ccctctcttt tctgcccag  ctgcccggca    5520 ctcttagcaa acctcaggca cccttacccc acatagacct ctgacagaga agcaggcact    5580
ttacatggag tcctggtggg agagccatag gctacggtgt aaaagaggca gggaagtggt    5640
ggtgtaggaa agtcaggact tcacatagaa gcctagccca caccagaaat gacagacaga    5700
tccctcctat ctcccccata agagtttgag tcgac                               5735
```

```
<210> SEQ ID NO 2
<211> LENGTH: 12
<212> TYPE: DNA
<213> ORGANISM: Artificial Sequence
<220> FEATURE:
<223> OTHER INFORMATION: Sequence inserted in promoter.

<400> SEQUENCE: 2
tgcatgccct ga                                                          12

<210> SEQ ID NO 3
<211> LENGTH: 12
<212> TYPE: DNA
<213> ORGANISM: Artificial Sequence
<220> FEATURE:
<223> OTHER INFORMATION: Sequence excised from promoter.

<400> SEQUENCE: 3
tatctgccca tc                                                          12

<210> SEQ ID NO 4
<211> LENGTH: 42
<212> TYPE: DNA
<213> ORGANISM: Artificial Sequence
<220> FEATURE:
<223> OTHER INFORMATION: Sequence inserted into promoter with TetO
      binding sites.

<400> SEQUENCE: 4
tcgagtttac cactccctat cagtgataga gaaaagtgaa ag                         42

<210> SEQ ID NO 5
<211> LENGTH: 627
<212> TYPE: DNA
<213> ORGANISM: Mus musculus
<220> FEATURE:
<221> NAME/KEY: CDS
<222> LOCATION: (21)...(602)
<223> OTHER INFORMATION: ELC1-a

<400> SEQUENCE: 5
```

```
gtcgacgagc ctaaagcaac atg cct ccc aag aaa ccc gag cct aag aag gag      53
                     Met Pro Pro Lys Lys Pro Glu Pro Lys Lys Glu
                      1               5                      10
act gcc aag ccg gct gca gcc cct gct cca gct gca tcc gca gcc ccg       101
Thr Ala Lys Pro Ala Ala Ala Pro Ala Pro Ala Ala Ser Ala Ala Pro
            15                  20                  25 gag ccc ctc aag gac tct gcc ttt gac cca aag agt gtg aag ata gac       149
Glu Pro Leu Lys Asp Ser Ala Phe Asp Pro Lys Ser Val Lys Ile Asp
        30                  35                  40 ttc agt gct gac cag atc gaa gaa ttc aaa gag gcc ttt tca ttg ttt       197
Phe Ser Ala Asp Gln Ile Glu Glu Phe Lys Glu Ala Phe Ser Leu Phe
    45                  50                  55 gac cgg act cca acg gga gag atg aag atc acc tac ggg cag tgt ggg       245
Asp Arg Thr Pro Thr Gly Glu Met Lys Ile Thr Tyr Gly Gln Cys Gly
60                  65                  70                  75 gac gtg ctg cgg gcc ctg ggc cag aac ccc acc aac gca gag gtg ctg       293
Asp Val Leu Arg Ala Leu Gly Gln Asn Pro Thr Asn Ala Glu Val Leu
                80                  85                  90 cgc gtt ttg ggc aaa ccc aag cct gaa gag atg agt tcc aag aca ctg       341
Arg Val Leu Gly Lys Pro Lys Pro Glu Glu Met Ser Ser Lys Thr Leu
            95                 100                 105 gac ttc gag atg ttc ctg ccc atc ctg caa cac atc tcc cgc aac aag       389
Asp Phe Glu Met Phe Leu Pro Ile Leu Gln His Ile Ser Arg Asn Lys
        110                 115                 120 gag cag ggc acc tat gag gac ttc gtg gag ggg ctg cgg gtc ttt gac       437
Glu Gln Gly Thr Tyr Glu Asp Phe Val Glu Gly Leu Arg Val Phe Asp
    125                 130                 135 aaa gaa agc aac ggc aca gtc atg ggt gcc gag ctt cgg cat gtc ctt       485
Lys Glu Ser Asn Gly Thr Val Met Gly Ala Glu Leu Arg His Val Leu
140                 145                 150                 155 gcc acc ctg gga gag aag atg agc gag gca gag gtg gag cag ctg ttg       533
Ala Thr Leu Gly Glu Lys Met Ser Glu Ala Glu Val Glu Gln Leu Leu
                160                 165                 170 tct ggg cag gag gat gcc aat ggc tgc atc aac tat gaa gcc ttt gtc       581
Ser Gly Gln Glu Asp Ala Asn Gly Cys Ile Asn Tyr Glu Ala Phe Val
            175                 180                 185 aag cac atc atg tct ggg taa agcacgtttc tccagggtgg tcgac             627
Lys His Ile Met Ser Gly *
        190

<210> SEQ ID NO 6
<211> LENGTH: 193
<212> TYPE: PRT
<213> ORGANISM: Mus musculus

<400> SEQUENCE: 6

Met Pro Pro Lys Lys Pro Glu Pro Lys Lys Glu Thr Ala Lys Pro Ala
 1               5                  10                  15

Ala Ala Pro Ala Pro Ala Ala Ser Ala Ala Pro Glu Pro Leu Lys Asp
            20                  25                  30

Ser Ala Phe Asp Pro Lys Ser Val Lys Ile Asp Phe Ser Ala Asp Gln
        35                  40                  45

Ile Glu Glu Phe Lys Glu Ala Phe Ser Leu Phe Asp Arg Thr Pro Thr
    50                  55                  60

Gly Glu Met Lys Ile Thr Tyr Gly Gln Cys Gly Asp Val Leu Arg Ala
65                  70                  75                  80

Leu Gly Gln Asn Pro Thr Asn Ala Glu Val Leu Arg Val Leu Gly Lys
                85                  90                  95

Pro Lys Pro Glu Glu Met Ser Ser Lys Thr Leu Asp Phe Glu Met Phe
            100                 105                 110
```

```
Leu Pro Ile Leu Gln His Ile Ser Arg Asn Lys Glu Gln Gly Thr Tyr
        115                 120                 125

Glu Asp Phe Val Glu Gly Leu Arg Val Phe Asp Lys Glu Ser Asn Gly
    130                 135                 140

Thr Val Met Gly Ala Glu Leu Arg His Val Leu Ala Thr Leu Gly Glu
145                 150                 155                 160

Lys Met Ser Glu Ala Glu Val Glu Gln Leu Leu Ser Gly Gln Glu Asp
                165                 170                 175

Ala Asn Gly Cys Ile Asn Tyr Glu Ala Phe Val Lys His Ile Met Ser
            180                 185                 190

Gly

<210> SEQ ID NO 7
<211> LENGTH: 1503
<212> TYPE: DNA
<213> ORGANISM: Mus musculus
<220> FEATURE:
<221> NAME/KEY: CDS
<222> LOCATION: (33)...(1295)
<223> OTHER INFORMATION: GSK-CA

<400> SEQUENCE: 7
cggacgcgtg gggtgattca agaagagcca tc atg tcg ggg cga ccg aga acc        53
                                   Met Ser Gly Arg Pro Arg Thr
                                     1               5 acc gcg ttt gcg gag agc tgc aag cca gtg cag cag cct tca gct ttt       101
Thr Ala Phe Ala Glu Ser Cys Lys Pro Val Gln Gln Pro Ser Ala Phe
         10                  15                  20 ggt agc atg aaa gtt agc aga gat aaa gat ggc agc aag gta acc aca       149
Gly Ser Met Lys Val Ser Arg Asp Lys Asp Gly Ser Lys Val Thr Thr
     25                  30                  35 gta gtg gca act cct ggc cag ggt cct gac agg cca cag gaa gtc agt       197
Val Val Ala Thr Pro Gly Gln Gly Pro Asp Arg Pro Gln Glu Val Ser
 40                  45                  50                  55 tat aca gac acg aaa gtg att gga aat gga tca ttt ggt gtg gta tat       245
Tyr Thr Asp Thr Lys Val Ile Gly Asn Gly Ser Phe Gly Val Val Tyr
                 60                  65                  70 caa gcc aaa ctt tgt gat tct gga gaa ctg gtt gcc atc aag aaa gtt       293
Gln Ala Lys Leu Cys Asp Ser Gly Glu Leu Val Ala Ile Lys Lys Val
             75                  80                  85 cta cag gac aag cga ttt aag aac cga gag ctc cag atc atg aga aag       341
Leu Gln Asp Lys Arg Phe Lys Asn Arg Glu Leu Gln Ile Met Arg Lys
         90                  95                 100 cta gac cac tgt aac ata gtc cga ctg cgg tat ttc ttc tac tcg agt       389
Leu Asp His Cys Asn Ile Val Arg Leu Arg Tyr Phe Phe Tyr Ser Ser
    105                 110                 115 ggt gag aag aaa gat gag gtc tac ctt aac ctg gtg ctg gac tat gtt       437
Gly Glu Lys Lys Asp Glu Val Tyr Leu Asn Leu Val Leu Asp Tyr Val
120                 125                 130                 135 ccg gag aca gtg tac aga gtc gcc aga cac tat agt cga gcc aag cag       485
Pro Glu Thr Val Tyr Arg Val Ala Arg His Tyr Ser Arg Ala Lys Gln
                140                 145                 150 aca ctc cct gtg atc tat gtc aag ttg tat atg tat cag ctg ttc aga       533
Thr Leu Pro Val Ile Tyr Val Lys Leu Tyr Met Tyr Gln Leu Phe Arg
            155                 160                 165 agt cta gcc tat atc cat tcc ttt gga atc tgc cat cga gac att aaa       581
Ser Leu Ala Tyr Ile His Ser Phe Gly Ile Cys His Arg Asp Ile Lys
        170                 175                 180 cca cag aac ctc ttg ttg gat cct gat aca gct gta tta aaa ctc tgt       629
```

|   |   |
|---|---|
| Pro Gln Asn Leu Leu Asp Pro Asp Thr Ala Val Leu Lys Leu Cys<br>185 190 195 | |
| gac ttt gga agt gca aag cag ctg gtc cga gga gag ccc aat gtt tca<br>Asp Phe Gly Ser Ala Lys Gln Leu Val Arg Gly Glu Pro Asn Val Ser<br>200 205 210 215 | 677 |
| tat atc tgt tct cgg tac tac agg gca cca gag ttg atc ttt gga gcc<br>Tyr Ile Cys Ser Arg Tyr Tyr Arg Ala Pro Glu Leu Ile Phe Gly Ala<br>220 225 230 | 725 |
| act gat tac acg tcc agt ata gat gta tgg tct gca ggc tgt gtg ttg<br>Thr Asp Tyr Thr Ser Ser Ile Asp Val Trp Ser Ala Gly Cys Val Leu<br>235 240 245 | 773 |
| gct gaa ttg ttg cta gga caa cca ata ttt cct ggg gac agt ggt gtg<br>Ala Glu Leu Leu Leu Gly Gln Pro Ile Phe Pro Gly Asp Ser Gly Val<br>250 255 260 | 821 |
| gat cag ttg gtg gaa ata ata aag gtc cta gga aca cca aca agg gag<br>Asp Gln Leu Val Glu Ile Ile Lys Val Leu Gly Thr Pro Thr Arg Glu<br>265 270 275 | 869 |
| caa att aga gaa atg aac cca aat tat aca gaa ttc aaa ttc cct caa<br>Gln Ile Arg Glu Met Asn Pro Asn Tyr Thr Glu Phe Lys Phe Pro Gln<br>280 285 290 295 | 917 |
| atc aag gca cat cct tgg aca aag gtc ttc cgg ccc cga act cca cca<br>Ile Lys Ala His Pro Trp Thr Lys Val Phe Arg Pro Arg Thr Pro Pro<br>300 305 310 | 965 |
| gag gca att gca ctg tgc agc cgt ctg ctg gag tac aca cct acc gcc<br>Glu Ala Ile Ala Leu Cys Ser Arg Leu Leu Glu Tyr Thr Pro Thr Ala<br>315 320 325 | 1013 |
| cgg cta aca cca ctg gaa gct tgt gca cat tca ttt ttc gat gaa ttg<br>Arg Leu Thr Pro Leu Glu Ala Cys Ala His Ser Phe Phe Asp Glu Leu<br>330 335 340 | 1061 |
| cgg gac cca aat gtc aaa cta cca aat ggg cga gac aca cct gca ctc<br>Arg Asp Pro Asn Val Lys Leu Pro Asn Gly Arg Asp Thr Pro Ala Leu<br>345 350 355 | 1109 |
| ttc aac ttt acc act caa gaa ctg tca agt aac ccc cct ctg gcc acc<br>Phe Asn Phe Thr Thr Gln Glu Leu Ser Ser Asn Pro Pro Leu Ala Thr<br>360 365 370 375 | 1157 |
| atc ctt atc cct cca cat gct cgg att cag gcc gct gct tca ccg cct<br>Ile Leu Ile Pro Pro His Ala Arg Ile Gln Ala Ala Ala Ser Pro Pro<br>380 385 390 | 1205 |
| gcc aac gcc aca gca gcc tca gat act aat gct gga gac cgt gga cag<br>Ala Asn Ala Thr Ala Ala Ser Asp Thr Asn Ala Gly Asp Arg Gly Gln<br>395 400 405 | 1253 |
| acc aat aac gcc gct tct gca tca gct tcc aac tcc acc tga<br>Thr Asn Asn Ala Ala Ser Ala Ser Ala Ser Asn Ser Thr *<br>410 415 420 | 1295 |
| acagccccca ggagccagct gcgcgggaaa gaccagcact tacttgagtg ccactcagca | 1355 |
| acactggtca cgtttggaaa gaaaattaaa aagaggaaaa caaaaacaaa aacaaaaaaa | 1415 |
| ccctgttcat tttagtgttc aatttttttt attgttgttc ttatttaacc ttgtaaaata | 1475 |
| tctatataaa tacaaaaaaa aaaaaaaa | 1503 |

<210> SEQ ID NO 8
<211> LENGTH: 420
<212> TYPE: PRT
<213> ORGANISM: Mus musculus

<400> SEQUENCE: 8

Met Ser Gly Arg Pro Arg Thr Thr Ala Phe Ala Glu Ser Cys Lys Pro
1               5                   10                  15

Val Gln Gln Pro Ser Ala Phe Gly Ser Met Lys Val Ser Arg Asp Lys

-continued

```
            20                  25                  30
Asp Gly Ser Lys Val Thr Thr Val Ala Thr Pro Gly Gln Gly Pro
        35                  40                  45
Asp Arg Pro Gln Glu Val Ser Tyr Thr Asp Thr Lys Val Ile Gly Asn
    50                  55                  60
Gly Ser Phe Gly Val Val Tyr Gln Ala Lys Leu Cys Asp Ser Gly Glu
65                  70                  75                  80
Leu Val Ala Ile Lys Lys Val Leu Gln Asp Lys Arg Phe Lys Asn Arg
                85                  90                  95
Glu Leu Gln Ile Met Arg Lys Leu Asp His Cys Asn Ile Val Arg Leu
            100                 105                 110
Arg Tyr Phe Phe Tyr Ser Ser Gly Glu Lys Lys Asp Glu Val Tyr Leu
            115                 120                 125
Asn Leu Val Leu Asp Tyr Val Pro Glu Thr Val Tyr Arg Val Ala Arg
        130                 135                 140
His Tyr Ser Arg Ala Lys Gln Thr Leu Pro Val Ile Tyr Val Lys Leu
145                 150                 155                 160
Tyr Met Tyr Gln Leu Phe Arg Ser Leu Ala Tyr Ile His Ser Phe Gly
                165                 170                 175
Ile Cys His Arg Asp Ile Lys Pro Gln Asn Leu Leu Leu Asp Pro Asp
            180                 185                 190
Thr Ala Val Leu Lys Leu Cys Asp Phe Gly Ser Ala Lys Gln Leu Val
        195                 200                 205
Arg Gly Glu Pro Asn Val Ser Tyr Ile Cys Ser Arg Tyr Tyr Arg Ala
    210                 215                 220
Pro Glu Leu Ile Phe Gly Ala Thr Asp Tyr Thr Ser Ser Ile Asp Val
225                 230                 235                 240
Trp Ser Ala Gly Cys Val Leu Ala Glu Leu Leu Leu Gly Gln Pro Ile
                245                 250                 255
Phe Pro Gly Asp Ser Gly Val Asp Gln Leu Val Glu Ile Ile Lys Val
            260                 265                 270
Leu Gly Thr Pro Thr Arg Glu Gln Ile Arg Glu Met Asn Pro Asn Tyr
        275                 280                 285
Thr Glu Phe Lys Phe Pro Gln Ile Lys Ala His Pro Trp Thr Lys Val
    290                 295                 300
Phe Arg Pro Arg Thr Pro Pro Glu Ala Ile Ala Leu Cys Ser Arg Leu
305                 310                 315                 320
Leu Glu Tyr Thr Pro Thr Ala Arg Leu Thr Pro Leu Glu Ala Cys Ala
                325                 330                 335
His Ser Phe Phe Asp Glu Leu Arg Asp Pro Asn Val Lys Leu Pro Asn
            340                 345                 350
Gly Arg Asp Thr Pro Ala Leu Phe Asn Phe Thr Thr Gln Glu Leu Ser
        355                 360                 365
Ser Asn Pro Pro Leu Ala Thr Ile Leu Ile Pro Pro His Ala Arg Ile
    370                 375                 380
Gln Ala Ala Ala Ser Pro Pro Ala Asn Ala Thr Ala Ala Ser Asp Thr
385                 390                 395                 400
Asn Ala Gly Asp Arg Gly Gln Thr Asn Asn Ala Ala Ser Ala Ser Ala
                405                 410                 415
Ser Asn Ser Thr
            420

<210> SEQ ID NO 9
```

-continued

```
<211> LENGTH: 32
<212> TYPE: DNA
<213> ORGANISM: Artificial Sequence
<220> FEATURE:
<223> OTHER INFORMATION: Primer used to amplify GSK

<400> SEQUENCE: 9
gtcgacaaga agagccatca tgtcggggcg ac                              32

<210> SEQ ID NO 10
<211> LENGTH: 62
<212> TYPE: DNA
<213> ORGANISM: Artificial Sequence
<220> FEATURE:
<223> OTHER INFORMATION: Primer used to amplify GSK

<400> SEQUENCE: 10
gtcgactgtt caagcgtagt ctgggacgtc gtatgggtag gtggagttgg aagctgatgc   60
ag                                                                  62
```

ROBUST, INDUCIBLE CARDIAC PREFERRED EXPRESSION SYSTEM FOR TRANSGENESIS

CROSS-REFERENCE TO RELATED APPLICATIONS

This application claims priority to, and the benefit of U.S. Provisional Patent Application No:60/393,525, filed on Jul. 3, 2002, which is incorporated herein by reference in its entirety.

FIELD OF THE INVENTION

The present invention relates to the field of regulation of tissue-preferred gene expression.

BACKGROUND OF THE INVENTION

A variety of human diseases and conditions manifested by cardiac abnormalities or cardiac dysfunction can lead to heart failure. Heart failure is a physiological condition in which the heart fails to pump enough blood to meet the circulatory requirements of the body. The study of such diseases and conditions in genetically diverse humans is difficult and unpredictable. Therefore, there is a need for a model system that facilitates the study of the mechanisms and causes of cardiac diseases and conditions as well as the identification of potential therapeutic targets.

The development of transgenic animal technology has provided significant advances for obtaining more complete information about complex systems in vivo. By manipulating the expression of a gene or genes in vivo, it is possible to gain insight into the roles of such genes in a particular system or to study aspects of the system in a genetically controlled environment.

While successful transgene experiments have been performed in a number of large and small animal species, the mouse has been the animal of choice for cardiovascular studies. See, for example, U.S. Pat. No. 6,353,151, herein incorporated by reference. Cardiac preferred transgenesis has been used to establish structure-function relationships between the presence or absence of a particular protein (or its mutated form) and normal or abnormal cardiac function at the molecular, cellular, and physiological levels. However, even with cardiac-preferred promoters, transgenesis can be a blunt instrument, particularly when studying powerful biological signaling proteins that in low abundance can have pleiotropic effects on cardiovascular structure, metabolism, and function. For example, the murine a-myosin heavy chain promoter initiates transcription in the early heart tube, as well as in the developing atria; thus transgene expression from the murine α-myosin heavy chain promoter throughout development has the potential of confounding the post-term phenotype.

Therefore, multiple laboratories have directed efforts at the development of conditional or inducible transgenic systems. One of the most widely used conditional systems is the binary, tetracycline-based system, which has been widely used in both cells and animals to reversibly induce expression by the addition or removal of tetracycline or its analogues. (See Bujard (1999). *J. Gene Med.* 1:372–374; Furth, et al. (1994). *Proc. Natl. Acad. Sci. USA* 91:9302–9306; and Mansuy & Bujard (2000). *Curr. Opin. Neurobiol.* 10:593–596, herein incorporated by reference in their entirety.)

Despite the potential advantages of the tetracycline target gene induction/inactivation system described above, few successes have been reported in the heart. The paucity of data from the cardiovascular system implies that the above described binary system is not robust in cardiac tissue and precludes routine success. Additionally, these systems require development of large numbers of transgenic lines to obtain a working pair of transgenics suitable for regulated, cardiac-preferred transgenic experiments. Furthermore, certain activator transgene constructs induce cardiopathic phenotypes in host animals, even when the animal does not contain a target transgene or responder construct. The presentation of a cardiopathic phenotype in the absence of target transgenes renders these animals less than ideal for use as transgenic models of cardiopathies and heart diseases.

Thus, development of a regulatable, transgenic model system is desirable for use in studying heart disease and conditions. It is of importance to develop a regulated, cardiac-preferred, transgenic expression system that allows controlled expression of a target transgene during any stage of development. It is of particular importance to develop a model transgenic system for studying cardiopathies.

SUMMARY OF THE INVENTION

Compositions and methods for cardiac-preferred expression of heterologous nucleotide sequences are provided. Compositions of the invention include novel nucleotide sequences for inducible, cardiac-preferred promoters; expression cassettes; vectors; host cells; animal cells; and animals, particularly transgenic mice comprising the nucleotide sequences of the invention. Expression cassettes, vectors, host cells, animal cells, and animals of the invention comprise an expression cassette comprising a nucleotide sequence of the invention operably linked to a nucleotide sequence of interest. In an embodiment the promoter is capable of initiating cardiac-preferred transcription, particularly ventricle-preferred transcription. In animals and transgenic mice of the invention, expression of a nucleotide sequence of interest is altered, particularly in cardiac tissue. In an embodiment, expression of the nucleotide sequence of interest is ventricle-preferred. In an embodiment, expression of the nucleotide sequence of interest is inducible. In an embodiment, the transgenic mouse's genome comprises an inducible promoter capable of initiating ventricle-preferred transcription operably linked to a nucleotide sequence of interest encoding a myocardial component. Transgenic mice comprising a nucleotide sequence of interest operably linked to a nucleotide sequence of the invention exhibit inducible altered expression of the nucleotide sequence of interest. In an embodiment, the transgenic mouse's genome comprises a nucleotide sequence of the invention operably linked to a nucleotide sequence encoding ELC1a. In an embodiment, the transgenic mouse's genome comprises a nucleotide sequence of the invention operably linked to a nucleotide sequence encoding a constitutively active form of GSK-3β.

The invention comprises a responder locus that is robustly inducible and minimally leaky. The responder locus is set forth in SEQ ID NO:1. The responder of the invention was derived from the mouse α-myosin heavy chain promoter sequence. The nucleotide sequence between nucleotides −3000 and −40 replaces five transcriptional regulatory cassettes. The resulting responder locus is a copy number dependent, position independent locus in which various transgenes of interest can be inserted. When uninduced, these transgenes are silent. When induced, the transgenes are very active. These genes can then be turned off using the inducible system.

Methods for altering expression of nucleotide sequences of interest in animals are provided. The animal's susceptibility to various cardiopathies, including but not limited to, cardiomyopathies, may be altered by the methods of the invention. Cardiomyopathies include, but are not limited to, familial hypertrophic cardiomyopathy, dilated cardiomyopathies, peripartum cardiomyopathy, and restrictive cardiomyopathies. In an embodiment, the animal exhibits increased susceptibility to cardiopathy. In one embodiment, the animal exhibits decreased susceptibility to cardiopathy. Expression cassettes comprising a promoter with a nucleotide sequence capable of initiating tissue-preferred, particularly cardiac-tissue preferred, transcription in the animal are developed. The promoter is operably linked to a heterologous nucleotide sequence of interest. An expression cassette comprising a nucleotide sequence of the invention capable of initiating cardiac-preferred expression operably linked to a heterologous nucleotide sequence of interest is used to generate a transgenic animal. The genome of the animal incorporates at least one expression cassette comprising the promoter and the nucleotide sequence of interest. Upon induction of the promoter, the nucleotide sequence of interest is preferentially expressed in a cardiac tissue. Inducible expression of the nucleotide sequence of interest occurs at detectable levels. In an embodiment the nucleotide sequence of interest encodes a myocardial component such as, but not limited to, α-myosin heavy chain, β-myosin heavy chain, essential myosin light chain-1, actin, catecholamine receptor, and glycogen synthase 3-β.

Methods for identifying anti-cardiopathic compounds are provided. In an embodiment, at least two transgenic mice whose genomes comprise at least one stably incorporated expression cassette comprising a nucleotide sequence of the invention operably linked to a heterologous nucleotide sequence of interest are provided. A compound is administered to the first mouse. The first and second mice are incubated for a period of time. A cardiopathic phenotype is monitored in both mice. Cardiopathic phenotypes include, but are not limited to, mortality, cardiac myocyte disarray, interstitial fibrosis, systolic dysfunction, diastolic dysfunction, left ventricular hypertrophy, cardiac mass abnormalities, right ventricular outflow tract obstruction, morphological changes, cellular degeneration, and hyper-contractility.

BRIEF DESCRIPTION OF THE DRAWINGS

FIG. 2, Panel B presents the results of a titration of doxycycline in the mouse diet. Lane 1 contains molecular weight markers. Lanes 2 and 3 contain protein from the atria and left ventricle of a nontransgenic control mouse. The transgenic line represented in Lane 4 contains the activator construct (tTA). The transgenic line represented in Lane 5 contains the responder construct operably linked to the ELC1a gene (MHCmin$^{TetO}$-ELC1a). The double transgenic line is represented in Lane 6. Lanes 7–9 contain protein obtained from heterozygous, double transgenic mice. The mice were fed the indicated levels of doxycycline for 3 weeks prior to harvest of the ventricle tissue. Lane 7, 100 mg doxycycline/kg chow; Lane 8, 200 mg doxycycline/kg chow; Lane 9, 625 mg doxycycline/kg chow.

Figure 1:
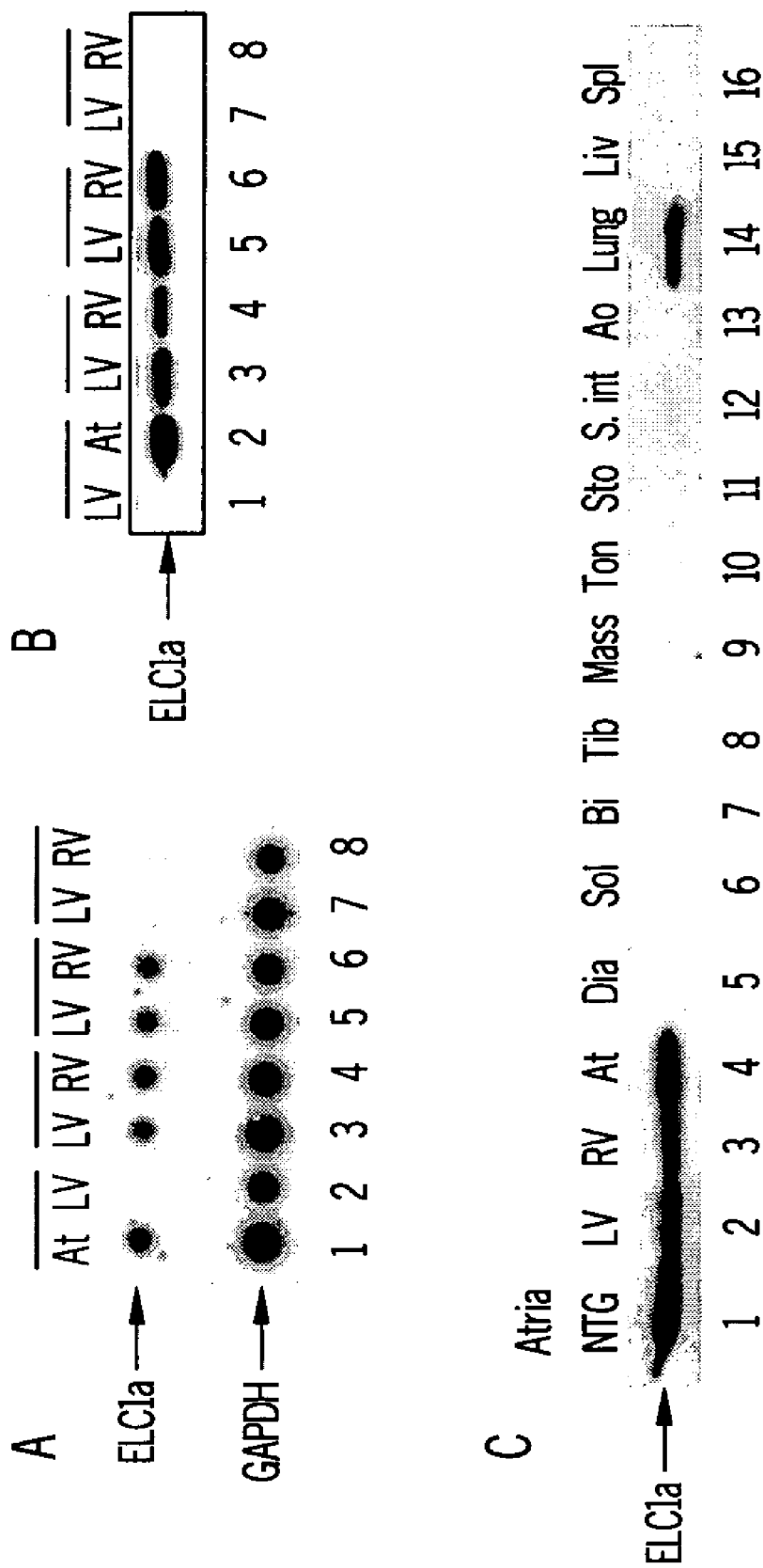
FIG. 1 depicts ventricle preferred expression of the atrial form of essential light chain-1 (ELC1a, SEQ ID NO:5) gene operably linked to a nucleotide sequence of the invention (SEQ ID NO:1). Panel A presents the results of a dot blot analysis of RNA isolated from a non-transgenic (NTG) control mouse and 3 lines of transgenic mice. 5 μg of RNA was blotted onto a nitrocellulose filter. The filter was hybridized to an ELC1a specific oligonucleotide probe. Glyceraldehyde 3-phosphate dehydrogenase (GAPDH) expression was used to normalize the data. Lanes 1 and 2 contain RNA isolated from atrial and left ventricular tissue, respectively. Lanes 3, 5, and 7 contain RNA isolated from left ventricular (LV) tissue. Lanes 4, 6, and 8 contain RNA isolated from right ventricular (RV) tissue. The three transgenic lines do not contain the activator construct. Panel B presents the results of Western analysis of protein expression in a non-transgenic mouse and 3 lines of transgenic mice. Lanes 1 and 2 contain proteins from atrial (lane 2) and ventricular (lane 1) tissue of a non-transgenic mouse. Lanes 3, 5, and 7 contain proteins from left ventricular (LV) tissue of three transgenic lines. Lanes 4, 6, and 8 contain proteins from the right ventricular (RV) tissue of the three transgenic lines. Panel C presents the results of Western analysis of atrial tissue from a non-transgenic mouse (lane 1) and various tissues from a transgenic line. Each lane contains 30 μg of protein from the following tissues: Lane 2, left ventricle (LV); Lane 3, right ventricle (RV); Lane 4, atria (At); Lane 5, diaphragm (Dia); Lane 6, soleus (Sol); Lane 7, bicep (Bi); Lane 8, tibialis (Tib); Lane 9, masseter (Mass); Lane 10, tongue (Ton); Lane 11, stomach (Sto); Lane 12, small intestine (S. int); Lane 13, aorta (Ao); Lane 14, lung; Lane 15, liver (Liv); and Lane 16, spleen (Spl). Lung tissue contains the pulmonary myocardium, derived from atrial tissue and consisting of a thin layer of atrial-like cells around a sub-population of the pulmonary veins and venules.

Panel A depicts the various protocol regimens. Animals subjected to protocol 1 underwent no doxycycline treatment. Animals subjected to protocol 2 were fed doxycycline for 4 weeks prior to TAC. After the TAC procedure, doxycycline was either withdrawn or maintained. Panel B depicts a time course of left ventricle mass to body mass ratio of animals that underwent either TAC or a sham procedure. Panel C depicts the left ventricle mass to body mass ratio from several mouse cohorts. Lanes 1–4 contain left ventricle:body mass ratios from nontransgenic mice (lane 1), mice containing the tTA activator construct (lane 2), mice containing the GSK-CA (constitutively active GSK-3β) responder construct (lane 3), and double transgenic mice containing the tTA activator construct and the GSK-CA responder construct (lane 4). Lane 5 depicts the left ventricle:body mass ratio of nontransgenic mice 2 weeks after the TAC procedure. Lane 6 depicts the left ventricle:body mass ratio of double transgenic mice 2 weeks after the TAC procedure. Lanes 7–9 depict the left ventricle:body mass ratios of mice 7 weeks after the TAC procedure. Lane 7 depicts the results from nontransgenic mice. Lane 8 depicts the results from double transgenic mice maintained on doxycycline. Lane 9 depicts the results from double transgenic mice withdrawn from doxycycline 1 week after the TAC procedure. Panel D presents the results of Western blot analysis of GSK-3β expression in protocol 2 mice. Protein samples were probed with either anti-GSK-3β antibodies or anti-hemaagluttinin antibodies. Lanes 1 and 2 depict the results obtained from non-transgenic mice in the absence and presence of doxycycline. Lanes 3–5 depict the results obtained from 3 double transgenic mice with doxycycline maintained in their feed. Lanes 6–8 depict the results obtained from 3 double transgenic mice from which doxycycline was withdrawn.

DETAILED DESCRIPTION OF THE INVENTION

The present invention provides for inducible cardiac-preferred expression of transgenes in animals. Compositions of the invention include isolated nucleic acid molecules, expression cassettes, vectors, host cells, and transgenic animals comprising the isolated nucleic acid molecules of the invention. The invention provides methods for altering expression of a nucleotide sequence of interest in an animal. Expression of the nucleotide sequences of interest may alter a transgenic animal's susceptibility to cardiopathies. Further, the invention provides methods for identifying anti-cardiopathic compounds.

The invention relates to compositions and methods drawn to regulatable cardiac-preferred promoters (SEQ ID NO:1) and methods of use. An animal cell or animal of the invention is stably transformed with an expression cassette comprising the cardiac-preferred promoter set forth in SEQ ID NO:1 operably linked to a nucleotide sequence of interest. The promoter sequences are useful for expressing operably linked sequences in a tissue-preferred, preferably cardiac-tissue preferred expression pattern. In an embodiment, the promoter is inducible.

As normally used in the whole animal, inducible expression depends upon a binary system and requires two transgenes. The two transgenes are an activator expression cassette and a target expression cassette comprising a target nucleotide sequence of interest operably linked to a responder promoter. Such animals can be provided through the construction of "double" transgenic animals, e.g., by mating two transgenic animals, one containing a target transgene encoding a selected protein and the other containing an activator transgene. Double transgenic systems are also used in cell culture. In cell culture systems, double transgenic cells are produced through any of several methods. The cells may be isolated from double transgenic animals or the two transgenes may be transformed into the cell. The transgenes may be transformed into the cells simultaneously or consecutively.

One example of such a binary system is the cre/loxP recombinase system of bacteriophage P1. For a description of the cre/loxP recombinase system, see, e.g., Lakso et al. (1992) *PNAS* 89:6232–6236. In the Cre/LoxP recombinase system, the activator transgene encodes recombinase. If a cre/loxP recombinase system is used to regulate expression of the transgene, animals containing transgenes encoding both the Cre recombinase and a selected target protein are required. Another example of a recombinase system is the FLP recombinase system of *S. cerevisiae* (O'Gorman et al. (1991) *Science* 251:1351–1355.

One of the most widely used inducible systems is the binary, tetracycline-based system, which has been used in both cells and animals to reversibly induce expression by the addition or removal of tetracycline or its analogues. (See Bujard (1999). *J. Gene Med.* 1:372–374; Furth, et al. (1994). *Proc. Natl. Acad. Sci. USA* 91:9302–9306; and Mansuy & Bujard (2000). *Curr. Opin. Neurobiol.* 10:593–596, herein incorporated by reference in their entirety.) Tetracycline analogs include, but are not limited to, doxycycline; demeclocycline; oxytetracycline; minocycline; autoclaved chlorotetracycline; vibramycin; lymecycline; DMG-minocycline; chemically modified tetracyclines such as CMT-5, CMT-3, and CMT-8; Col3; and glycylcyclines such as GAR-936 and 9-(N-N-dimethylglycylamide) 6 dimethyl 6 deoxytetracycline.

In the tetracycline based system, the two transgenes are 1) a cardiac-preferred promoter driving the tet-controlled transactivator (tTA) sequence coupled to the transcription activator protein VP-16, and 2) a responder promoter consisting of the cytomegalovirus minimal promoter coupled to 5–7 copies of the tet operon (tetO). For cardiac-preferred expression, a cardiac-preferred promoter such as the α-myosin heavy chain promoter, controls expression of the tTA protein. The responder promoter is then operably linked to the target transgene that is to be conditionally controlled. In the presence of tetracycline or an analogue thereof, the tTA protein binds to the drug and transcription of the target transgene occurs only from the responder promoter. If the drug is not present in the system, tTA binds the tetO sequences allowing the VP16 transactivator protein to increase expression driven by the minimal promoter. In an embodiment, the isolated nucleic acid molecule of the invention is an inducible, cardiac-preferred responder promoter.

By "inducible" is intended that a chemical stimulus alters expression of the operably linked nucleotide sequence of interest by at least 1%, 5%, preferably 10%, 20%, more preferably 30%, 40%, 50%, 60%, 70%, 80%, 90%, 99% or more. The difference may be an increase or decrease in expression levels. Methods for assaying expression levels are described elsewhere herein. The chemical stimulus may be administered or withdrawn. Various chemical stimuli are known in the art. In an embodiment, the chemical stimulus is tetracycline, or an analog thereof.

By "stably transformed" is intended that the nuclear genome of the animal cell or the nuclear genome of at least one cell of the animal has incorporated at least one copy of the transgene. A transgenic animal of the invention comprises at least one stably transformed cell comprising the nucleotide sequence of interest. In an embodiment, the genome of a germ-line cell of a transgenic animal comprises the nucleotide sequence of interest. The invention encompasses isolated or substantially purified nucleic acid or protein compositions. An "isolated" or substantially "purified" nucleic acid molecule, or biologically active portion thereof, is substantially free of other cellular material, or culture medium when produced by recombinant techniques or substantially free of chemical precursors or other chemicals when chemically synthesized. Preferably, an "isolated" nucleic acid molecule is free of sequences (preferably polypeptide encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Methods for isolation of promoter regions are well known in the art. By "isolated" is intended that the promoter sequences have been determined and can be extracted by molecular techniques or synthesized by chemical means. In either instance, the promoter is removed from at least one of its flanking sequences in its native state.

Fragments and variants of the disclosed nucleotide sequence are also encompassed by the present invention. By "fragment" is intended a portion of the nucleotide sequence. Fragments of a nucleotide sequence may retain biological activity and drive expression, particularly cardiac-preferred expression, more particularly ventricle-preferred expression, and yet more particularly inducible, cardiac-preferred expression. Alternatively, fragments of a nucleotide sequence that are useful as hybridization probes generally do not retain biological activity. Thus, fragments of a nucleotide sequence may range from at least about 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, up to about 5735 nucleotides for SEQ ID NO:1.

Thus a fragment of a nucleotide sequence for inducible, cardiac-preferred promoters may encode a biologically active portion of an inducible, cardiac tissue-preferred promoter, or it may be a fragment that can be used as a hybridization probe or PCR primer using methods disclosed below. A biologically active portion of an inducible, cardiac tissue preferred promoter can be prepared by isolating a portion of the promoter nucleotide sequence disclosed herein, and assessing the activity of the portion of the promoter. Nucleic acid molecules that are fragments of an inducible, cardiac-preferred promoter comprise 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, up to about 5735 nucleotides for SEQ ID NO:1.

By "variants" is intended substantially similar sequences. For nucleotide sequences, naturally occurring variants can be identified with the use of well-known molecular biology techniques, as, for example, with polymerase chain reactions (PCR) and hybridization techniques as outlined below. Variant nucleotide sequences also include synthetically derived nucleotide sequences, such as those generated for example, by using site-directed mutagenesis. Generally, variants of a particular nucleotide sequence of the invention will have at least 95%, 96%, 97%, and preferably 98%, 99%, or more sequence identity to that particular nucleotide sequence as determined by sequence alignment programs described elsewhere herein using default parameters. Methods for mutagenesis and nucleotide sequence alterations are well known in the art. See, for example, Kunkel (1985) *Proc. Natl. Acad. Sci.* USA 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Co., New York) and the references cited therein.

Variant nucleotide sequences also encompass sequences derived from a mutagenic and recombinogenic procedure such as DNA shuffling. With such a procedure, one or more different promoter sequences including the promoter sequences disclosed herein, can be manipulated to create a new promoter sequence possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci.* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci.* 94:4504–4509; Crameri et al. (1998) *Nature* 391:288–291; Miyazaki (2002) *Nucleic Acids Research* 30:E139–9; Song et al. (2002) *Appl. Environ. Microbiol.* 68:6146–51; Hayes et al. (2002) *Proc. Natl. Acad. Sci.* 99:15926–31; Coco et al. (2001) *Nature Biotechnol.* 19:354–9; Kikuchi et al. (2000) *Gene* 243:133–7; and U.S. Pat. Nos. 5,606,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

(b) As used herein "comparison window" makes reference to a contiguous and specified segment of a polynucleotide sequence, wherein the polynucleotide sequence in the comparison window may comprise additions or deletions (i.e. gaps) compared to the reference sequence (which does not comprise additions or deletions) for optimal alignment of the two sequences. Generally the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) CABIOS 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. For purposes of the present invention, comparison of nucleotide or protein sequences for determination of percent sequence identity to the sequences disclosed herein is preferably made using the GCG program GAP (Version 10.00 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Sequence comparison programs include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences disclosed herein can be used to identify corresponding sequences in cells, tissues, and animals. In this manner, methods such as PCR, hybridization, and the like can be used to identify such sequences based on their sequence homology to the sequences set forth herein. These techniques may be used as a diagnostic assay to determine the presence of the promoter sequences of the invention in an animal or animal cell.

In a PCR approach, oligonucleotide primers can be designed for use in PCR reactions to amplify corresponding DNA sequences from cDNA or genomic DNA extracted from any animal of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the promoter sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire promoter sequence disclosed herein, or one or more portions thereof, may be used as a probe capable of specifically hybridizing to corresponding promoter sequences. To achieve specific hybridization under a variety of conditions, such probes include sequences that are unique among inducible, cardiac-preferred promoter sequences and are preferably at least about 10 nucleotides in length, and most preferably at least about 20 nucleotides in length. Such probes may be used to amplify corresponding promoter sequences from a chosen animal by PCR.

Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m = 81.5°$ C. $+16.6$ (log M)$+0.41$ (% GC)$-0.61$(% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, T$_m$, hybridization, and/or wash conditions can be adjusted to hybridize to sequences of the desired identity. For example, if sequences with approximately 90% identity are sought, the T$_m$ can be decreased 10° C. Generally, stringent conditions are selected to be about 5° C. lower than the thermal melting point (T$_m$) for the specific sequence and its complement at a defined ionic strength and pH. However, severely stringent conditions can utilize a hybridization and/or wash at 1, 2, 3, or 4° C. lower than the thermal melting point (T$_m$); moderately stringent conditions can utilize a hybridization and/or wash at 6, 7, 8, 9, or 10° C. lower than the thermal melting point (T$_m$); low stringency conditions can utilize a hybridization and/or wash at 11, 12, 13, 14, 15, or 20° C. lower than the thermal melting point (T$_m$). Using the equation, hybridization and wash compositions, and desired T$_m$, those of ordinary skill will understand that variations in the stringency of hybridization and/or wash solutions are inherently described. If the desired degree of mismatching results in a T$_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.). Thus, isolated sequences that have promoter activity and which hybridize under stringent conditions to the inducible, cardiac-preferred promoter sequences disclosed herein, or to fragments thereof, are encompassed by the present invention. Such sequences will be at least 95%, 96%, 97%, 98% to 99% homologous or more with the disclosed sequences. That is, the sequence identity of sequences may range, sharing at least 95%, 96%, 97%, 98%, 99% or more sequence identity.

It is recognized that any nucleotide sequence of interest can be operably linked to a promoter of the invention and expressed in cardiac tissue. By "cardiac tissue" is intended any tissue obtained from the heart, including but not limited to, tissues developmentally related to the heart such as the pulmonary myocardium. By "ventricle tissue" is intended any tissue obtained from any portion of either ventricle of the heart.

General categories of nucleotide sequences of interest for the purposes of the present invention include for example, those genes involved in information, such as Zinc fingers, those involved in communication, such as kinases, and those involved in housekeeping, such as heat shock proteins. For example, nucleotide sequences of interest include but are not limited to those encoding, serine-threonine kinases, potassium channel genes, nitric oxide synthases, glycoprotein receptors, class 1 HLA, class 2 HLA, cathepsin B, cysteine aminopeptidases, acid gelatinases, trypsin-like endopeptidases, chymotrypsin-like endopeptidases, neutral gelatinases, angiotensin type-II receptors, myocardial sarcoplasmic reticulum Ca$^{2+}$-ATPase, troponin T, troponin I, α-tropomyosin, TGF-β1, IGF-I, IGF-II, PDGF-B, GSK-3β, prorenin, rennin, myosin binding protein C, ion channel genes, retinoic acid receptors, α-myosin heavy chains, β-myosin heavy chains, essential myosin light chains, actins, sarcomere components, chaperones, elements of the apoptotic pathway, and elements of the cytoskeleton including, but not limited to, desmins.

The nucleotide sequence of interest expressed by the promoters of the invention may be used for varying the phenotype of the heart. Various phenotypes of interest in cardiac tissue include, but are not limited to, hypertrophy; morphology, such as interventricular septal thickness; left ventricular-end systolic or end-diastolic dimensions; papillary muscle dimension; left-ventricular outflow tract obstruction; sarcomere structure, particularly alterations resulting in familial hypertrophic cardiomyopathy; alteration of myosin isoform expression, particularly resulting in altered susceptibility to cardiopathies; myofibril function; cardiopathic susceptibility; responsiveness to anti-cardiopathic compounds; receptor expression; heart rate; ventricular systolic pressure, ventricular diastolic pressure; aortic systolic pressure; aortic diastolic pressure; contractility; interstitial fibrosis; cardiomyocyte disarray; Ca$^{2+}$ sensitivity; catecholine sensitivity; α-adrenergic sensitivity; beta-adrenergic sensitivity; angiotensin-converting enzyme inhibitor sensitivity; amiodarone sensitivity; lidocaine sensitivity; glycoprotein receptor antagonist sensitivity; anabolic steroid sensitivity; cell death; cell type plasticity; and the like.

These results can be achieved by providing expression of heterologous products or increased expression of endogenous products in cardiac tissue. Alternatively, the results can be achieved by providing for a reduction of expression of one or more endogenous products, particularly enzymes and cofactors in the cardiac tissue. These changes result in a change in phenotype of the transgenic animal. For example, the promoter sequences of the invention can be used to preferentially express ELC1a (essential light chain 1, atrial isoform) in the ventricles and alter the ELC1 isoform expression pattern. In an embodiment, the promoter sequences of the invention can be used to express a serine-threonine kinase such as GSK-3β or a constitutively active form of GSK-3β such as GSK-CA. Alternatively, the promoter sequences of the invention can be used to produce antisense mRNA complementary to the coding sequence of a cardiac protein, inhibit production of the protein, and alter expression of the heterologous nucleotide sequence. Alternatively, the promoter sequences of the invention can be used to produce small interfering RNAs.

Products of the heterologous nucleotide sequence include structural proteins, enzymes, cofactors, hormones, signaling proteins, and the like.

As noted, the heterologous nucleotide sequence operably linked to one of the promoters disclosed herein may be an antisense sequence for a targeted gene. Thus, with these promoters, antisense constructions complementary to at least a portion of the messenger RNA (mRNA) for a targeted sequence sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in cardiac tissue.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region. Thus, the promoter regions disclosed herein are generally further defined by comprising upstream regulatory elements such as those responsible for tissue and temporal expression of the coding sequence, enhancers and the like. Such elements are typically linked via a 5' untranslated region, which may further modulate gene expression, to a coding region of interest. In the same manner, the promoter elements that enable expression in the desired tissue such as cardiac-tissue can be identified, isolated, and used with other core promoters to confirm cardiac-preferred expression. For genes in which the 5' untranslated region does not affect cell specificity, alternative sources of 5' untranslated leaders may be used in conjunction with these promoter elements.

The regulatory sequences of the present invention, when operably linked to a heterologous nucleotide sequence of interest and inserted into an expression vector, enable inducible cardiac-preferred expression of the nucleotide sequence of interest in the cardiac tissue of an animal stably transformed with this expression vector. By "cardiac-preferred" is intended that expression of the heterologous sequence is most abundant in cardiac tissue, while some expression may occur in other tissue types, particularly in tissues developmentally related to cardiac tissue. Cardiac-preferred expression of a heterologous nucleotide sequence of interest occurs at levels at least 1%, 5%, preferably 10%, 20%, more preferably 30%, 40%, 50%, 60%, 70%, 80%, 90%, 100% or more than expression of the nucleotide sequence of interest in non-cardiac tissue. By "ventricle-preferred" is intended that expression of the heterologous sequence is most abundant in ventricle tissues, while some expression may occur in other tissue types. Ventricle-preferred expression of a nucleotide sequence of interest occurs at levels at least 1%, 5%, preferably 10%, 20%, more preferably 30%, 40%, 50%, 60%, 70%, 80%, 90%, 100% or more than expression of the heterologous nucleotide sequence of interest in non-ventricular tissue. In an embodiment, ventricle-preferred expression of a heterologous nucleotide sequence natively expressed in atrial tissue may be desired. Expression of a heterologous nucleotide sequence from a ventricle-preferred promoter may not impact atrial expression of the nucleotide sequence operably linked to its native promoter. By "atria-preferred" is intended that expression of the heterologous sequence is most abundant in atrial tissues, while some expression may occur in other tissue types. Atria-preferred expression of a heterologous nucleotide sequence occurs at levels at least 1%, 5%, preferably 10%, 20%, more preferably 30%, 40%, 50%, 60%, 70%, 80%, 90%, 100% or more than expression of the heterologous nucleotide sequence in non-atrial tissue.

By "heterologous nucleotide sequence" is intended a sequence that is not naturally occurring with the promoter sequence. While this nucleotide sequence is heterologous to the promoter sequence, it may be homologous, or native, or heterologous, or foreign, to the animal host.

It is recognized that the promoters may be used with their native coding sequences to increase or decrease expression resulting in a change in phenotype in the cardiac tissue of the transformed animal.

The isolated promoter sequences of the present invention can be modified to provide for a range of expression levels of the heterologous nucleotide sequence. Thus, less than the entire promoter regions may be utilized and the ability to drive inducible, cardiac-preferred expression retained. However, it is recognized that expression levels of mRNA may be altered and usually decreased with deletions of portions of the promoter sequences. Generally, at least about 20 nucleotides of an isolated promoter sequence will be used to drive expression of a nucleotide sequence.

It is recognized that to increase transcription levels or to alter tissue specificity, enhancers and/or tissue-preference elements may be utilized in combination with the promoter regions of the invention. For example, quantitative or tissue specificity upstream elements from other cardiac-preferred promoters may be combined with the promoter regions of the invention to augment cardiac-preferred transcription. Such elements have been characterized, for example, the murine TIMP-4 promoter (Rahkonen, et al. (2002) *Biochim Biophys Acta* 1577:45–52), A and B-type natriuretic peptide promoters (Grepin et al. (1994) *Mol. Cell Biol.* 14:3115–29), human cardiac troponin I promoter (Dellow, et al. (2001) *Cardiovasc. Res.*50:3–6), mouse S100A1 promoter (Kiewitz, et al. (2000) *Biochim Biophys Acta* 1498:207–19), salmon cardiac peptide promoter (Majalahti-Palviainen, et al (2000) *Endocrinology* 141:731–740), GATA response element (Charron et al. (1999) *Molecular & Cellular Biology* 19:4355–4365) and the like, herein incorporated by reference.

Other enhancers are known in the art that would alter the tissue specificity by driving expression in other tissues in addition to cardiac tissue, such as in skeletal tissue, CNS tissue, pulmonary tissue, salivary tissue, lacrimal tissue, and vascular tissue, among others. These include, for example, upstream elements from the promoter of the aquaporin-5 promoter (Borok, et al. (2000) *J. Biol. Chem.* 275:26507–14, herein incorporated by reference) that would give pulmonary and salivary-preferred expression in addition to cardiac-preferred expression. Another example includes upstream elements from the human alpha-skeletal actin promoter, which would give expression in skeletal muscle, in addition to cardiac-preferred expression.

Modifications of the isolated promoter sequences of the present invention can provide for a range of expression of the heterologous nucleotide sequence. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts; conversely, a strong promoter drives expression of a coding sequence at a high level, or at about 1/10 transcripts to about 1/100 transcripts to about 1/1000 transcripts.

The nucleotide sequences for the cardiac-preferred promoter disclosed in the present invention, as well as variants and fragments thereof, are useful in the genetic manipulation of any animal when operably linked with a heterologous nucleotide sequence whose expression is to be controlled to achieve a desired phenotypic response. By "operably linked" is intended the transcription of the heterologous nucleotide sequence is under the influence of the promoter sequence. In this manner, the nucleotide sequences for the promoters of the invention may be provided in expression cassettes along with heterologous nucleotide sequences for expression in the animal of interest, more particularly in the heart of the animal.

Such expression cassettes will comprise a transcriptional initiation region comprising one of the promoter nucleotide sequences of the present invention, or variants or fragments thereof, operably linked to the nucleotide sequence of interest whose expression is to be controlled by the cardiac-preferred promoters disclosed herein. Such an expression cassette is provided with at least one restriction site for insertion of the nucleotide sequence to be under the transcriptional regulation of the regulatory regions. The expression cassette may additionally contain selectable marker genes.

The expression cassette will include in the 5'-to-3' direction of transcription, a transcriptional and translational initiation region, and a heterologous nucleotide sequence of interest. In addition to containing sites for transcription initiation and control, expression cassettes can also contain sequences necessary for transcription termination and, in the transcribed region a ribosome-binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

The expression cassette comprising the promoter sequence of the present invention operably linked to a heterologous nucleotide sequence may also contain at least one additional nucleotide sequence for a gene to be co-transformed into the organism. Alternatively, the additional sequence(s) can be provided on another expression cassette.

The regulatory sequences to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

Where appropriate, the heterologous nucleotide sequence whose expression is to be under the control of the promoter sequence of the present invention and any additional nucleotide sequence(s) may be optimized for increased expression in the transformed animal. That is, these nucleotide sequences can be synthesized using species preferred codons for improved expression, such as mouse-preferred codons for improved expression in mice. Methods are available in the art for synthesizing species-preferred nucleotide sequences. See, for example, Wada et al. (1992) *Nucleic Acids Res.* 20 (Suppl.), 2111–2118; Butkus et al. (1998) *Clin Exp Pharmacol Physiol Suppl.* 25:S28–33; and Sambrook et al. (1989) *Molecular Cloning: A Laboratory Manual* 2nd. ed., Cold Spring Harbor Laboratory Press, Cold Spring Harbor, N.Y., herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); and human immunoglobulin heavy-chain binding protein (BiP) (Macejak et al. (1991) *Nature* 353: 90–94). Other methods known to enhance translation and/or mRNA stability can also be utilized, for example, introns, and the like.

In those instances where it is desirable to have the expressed product of the heterologous nucleotide sequence directed to a particular organelle, particularly the mitochondria, the nucleus, the endoplasmic reticulum, or the Golgi apparatus; or secreted at the cell's surface or extracellularly; the expression cassette may further comprise a coding sequence for a transit peptide. Such transit peptides are well known in the art and include, but are not limited to, the transit peptide for the acyl carrier protein, the small subunit of RUBISCO, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose; in vitro mutagenesis; primer repair; restriction; annealing; substitutions, for example, transitions and transversions; or any combination thereof may be involved.

Reporter genes or selectable marker genes may be included in the expression cassettes. Examples of suitable reporter genes known in the art can be found in, for example, Ausubel et al. (2002) *Current Protocols in Molecular Biology*. John Wiley & Sons, New York, N.Y., herein incorporated by reference.

Selectable marker genes for selection of transformed cells or tissues can include genes that confer antibiotic resistance. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108: 219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Biol.* 15:127–136); puromycin (Abbate et al (2001) *Biotechniques* 31:336–40; cytosine arabinoside (Eliopoulos et al. (2002) *Gene Ther.* 9:452–462); 6-thioguanine (Tucker et al. (1997) *Nucleic Acid Research* 25:3745–46).

Other genes that could serve utility in the recovery of transgenic events but might not be required in the final product would include, but are not limited to, examples such as GUS (b-glucoronidase; Jefferson (1987) *Plant Mol. Biol. Rep.* 5:387); GFP (green fluorescence protein; Wang et al. (2001) *Anim Biotechnol* 12:101–110; Chalfie et al. (1994) *Science* 263:802), BFP (blue fluorescence protein; Yang et al. (1998) *J. Biol. Chem.* 273:8212–6), CAT; and luciferase (Riggs et al. (1987) *Nucleic Acid Res.* 15 (19):8115; Luchrsen et al. (1992) *Methods Enzymol.* 216: 397–414).

Any of the regulatory or other sequences useful in expression vectors can form part of the transgenic sequence. This includes intronic sequences and polyadenylation signals, if not already included. In one embodiment, the animal cell can be a fertilized oocyte or embryonic stem cell that can be used to produce a transgenic animal comprising at least one stably transformed expression cassette comprising the nucleotide sequence of interest. Alternatively, the host cell can be a stem cell or other early tissue precursor that gives rise to a specific subset of cells and can be used to produce transgenic tissues in an animal. See also Thomas et al., (1987) *Cell* 51:503 for a description of homologous recombination vectors. The vector is introduced into an embryonic stem cell line (e.g., by electroporation) and cells in which the introduced gene has recombined with the genome are selected (see e.g., Li, E. et al. (1992) *Cell* 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the recombined DNA in their germ cells can be used to breed animals in which all cells of the animal contain the recombined DNA by germ line transmission of the transgene. Methods for constructing homologous recombination vectors and homologous recombinant animals are described further in Bradley, A. (1991) Current Opinion in Biotechnology 2:823–829 and in PCT International Publication Nos. WO 90/11354; WO 91/01140; and WO 93/04169, herein incorporated by reference in their entirety.

The genetically engineered host cells can be used to produce non-human transgenic animals. A transgenic animal is preferably a mammal, for example a mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. The transgenic animals of the invention are useful for studying the function of a cardiac component and identifying and evaluating modulators of cardiopathic phenotypes.

Methods for generating transgenic animals via embryo manipulation and microinjection, particularly animals such as mice, have become conventional in the art and are described, for example, in U.S. Pat. Nos. 4,736,866; 4,870,009; 4,873,191; and in Hogan, B., Manipulating the Mouse Embryo, (Cold Spring Harbor Laboratory Press, Cold Spring Harbor, N.Y., 1986), herein incorporated by reference in their entirety.

Similar methods are used for production of other transgenic animals. A transgenic animal can be produced by introducing nucleic acid into the male pronuclei of a fertilized oocyte, e.g., by microinjection, retroviral infection, and allowing the oocyte to develop in a pseudopregnant female foster animal. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Other examples of transgenic animals include non-human primates, sheep, dogs, pigs, cows, goats, rabbits, and rats. Methods for providing transgenic rabbits are described in Marian et al. (1999) *J. Clin. Invest.* 104:1683–1692 and James et al. (2000) *Circulation* 101:1715–1721, herein incorporated by reference in their entirety.

In an embodiment, the invention provides a method of altering expression of a nucleotide sequence of interest in an animal, particularly of altering cardiac-preferred expression of the nucleotide sequence of interest. In the method the nucleotide sequence of interest is operably linked to an inducible, cardiac preferred promoter such as the nucleotide sequence presented in SEQ ID NO:1. An expression cassette comprising the cardiac preferred promoter operably linked to the nucleotide sequence of interest is used to transform an animal. Animal transformation methods are known in the art and reviewed elsewhere herein. Transgenic animals are identified by methods known to one skilled in the art including, but not limited to, Southern blots, PCR, and hybridization methods. Single transgenic animals with the desired inducible cardiac-preferred expression pattern can be identified by methods known to one skilled in the art including, but not limited to, RNA dot blots, Northern blots, RT-PCR, Western blots, and Taqman analysis. Single transgenic animals with the desired expression patterns are mated with transgenic animals comprising an activator transgene such as, but not limited to, the αMHC-tTA construct described elsewhere herein. The method yields a stably transformed transgenic animal exhibiting altered expression of a nucleotide sequence of interest.

By "altered cardiac-preferred expression" is intended that the expression of the heterologous nucleotide sequence in a transgenic cell or cardiac tissue of a transgenic animal of the invention differs from expression levels in a non-cardiac cell or cardiac tissue of a non-transgenic animal by at least 1%, 5%, preferably 10%, 20%, more preferably 30%, 40%, 50%, 60%, 70%, 80%, 90%, 99% or more. The difference may be an increase or decrease in expression levels.

Methods of determining expression levels are known in the art and include, but are not limited to, qualitative Western blot analysis, immunoprecipitation, radiological assays, polypeptide purification, spectrophotometric analysis, Coomassie staining of acrylamide gels, ELISAs, RT-PCR, 2-D gel electrophoresis, microarray analysis, in situ hybridization, chemiluminescence, silver staining, enzymatic assays, ponceau S staining, multiplex RT-PCR, immunohistochemical assays, radioimmunoassay, colorimetric analysis, immunoradiometric assays, positron emission tomography, Northern blotting, fluorometric assays and SAGE. See, for example, Ausubel et al, eds. (2002) Current Protocols in Molecular Biology, Wiley-Interscience, New York, N.Y.; Coligan et al (2002) Current Protocols in Protein Science, Wiley-Interscience, New York, N.Y.; and Sun et al. (2001) *Gene Ther.* 8:1572–1579, herein incorporated by reference. Analysis of GSK-3β and ELC1 isoform expression are described elsewhere herein.

GSK-3β is a serine/threonine kinase that may affect cellular processes including, but not limited to, development, differentiation, and proliferation. When dephosphorylated at serine 9, the kinase activity of GSK-3β is constitutively active. A nucleotide sequence (SEQ ID NO:7) encoding a constitutively active form of GSK-3β, GSK-CA (SEQ ID NO:8) was operably linked to a promoter of the invention as described elsewhere herein.

By "kinase activity" is intended phosphorylation of a substrate such as, but not limited to, an amino acid, polypeptide, or protein. It is recognized that the present invention is not dependent upon a particular mechanism of phosphorylation. Rather the kinase activity of the GSK-3β of a mouse of the invention increases the phosphorylation of a substrate independently of how that phosphorylation is increased or achieved.

Methods of assaying kinase activity are known in the art and include, but are not limited to, immunoprecipitation with antibodies to phospho-amino acids such as phosphoserine or phosphothreonine; fluorescence polarization; filter binding assays with radioisotopes, scintillation proximity assays, 96 well assays with conjugated antibodies; time resolved fluorescent assays, thin layer chromatography; immunoprecipitation and immune complex assays; nontrichloroacetic acid phosphoamino acid determinations; protein kinase assays; SAPK/Jun kinase activity assays; and tyrosine kinase activity assays. See U.S. Patent Application No:20030036106; U.S. Pat. No:5,447,860; Walker, John, ed. (2002) *Protein Protocols on CD-ROM* v. 2; and Ausubel et al., eds. (1995) *Current Protocols in Molecular Biology*, (Greene Publishing and Wiley-Interscience, New York); herein incorporated by reference in their entirety.

A nucleotide sequence (SEQ ID NO:5) encoding ELC1a (SEQ ID NO:6) was operably linked to a promoter of the invention as described elsewhere herein. ELC1a is the atrial isoform of essential myosin light chain 1, an abundant contractile polypeptide. The various ELC1 isoforms affect cardiac muscle contractility. Essential myosin light chains such as ELC1a are associated with the neck region of the myosin heavy chain. ELC1a is capable of associating with cardiac myosin heavy chain. ELC1a is thought to interact with actin and may affect myosin-actin cross-bridge cycling. Further, ELC1a may modulate cardiac systolic and diastolic function. See Sanbe et al. (2001) *J. Biological Chemistry* 276:32682–32686, herein incorporated by reference in its entirety.

Methods of analyzing ELC1a association with cardiac myosin heavy chain are known in the art and include, but are not limited to, X-ray crystallography, NMR, ultracentrifugation, immunoprecipitation, co-immunoprecipitation, crosslinking, yeast two-hybrid assays, and affinity chromatography. See for example Walker, John, ed. (2002) *Protein Protocols on CD-ROM* v. 2; and Ausubel et al., eds. (1995) *Current Protocols in Molecular Biology*, (Greene Publishing and Wiley-Interscience, New York); herein incorporated by reference in their entirety.

Transgenic animals that exhibit altered cardiac preferred expression of the nucleotide sequence of interest are useful to conduct assays that identify compounds that affect cardiac function. The altered cardiac-preferred expression of the heterologous nucleotide sequence may result in altered susceptibility to a cardiopathy.

A "cardiopathy" is any disorder or condition involving the heart or cardiac tissue. Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy; hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; Brock's disease, neoplastic heart disease, including but not limited to, primary cardiac tumors, such as myxoma, lipoma, papillary fibroelastoma, rhabdomyoma, and sarcoma, and cardiac effects of noncardiac neoplasms, congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia; disorders involving cardiac transplantation; myocardial stunning; arterial hypertension; peripartum cardiomyopathy; alcoholic cardiomyopathy; supraventricular tachycardia, bradycardia; atrial flutter; hydrops fetalis; extrasystolic arrhythmia; fetal cardiac arrhythmia; endocarditis; atrial fibrillation; idiopathic dilated cardiomyopathy; Chagas' heart disease; long QT syndrome; and Brugada syndrome.

A "cardiomyopathy" is any disorder or condition involving cardiac muscle tissue. Disorders involving cardiac muscle tissue include, but are not limited to, myocardial disease, including but not limited to dilated cardiomyopathy, hypertrophic cardiomyopathy, restrictive cardiomyopathy, myocardial stunning, and myocarditis; rheumatic fever; rhabdomyoma; sarcoma; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia; disorders involving cardiac transplantation; arterial hypertension; peripartum cardiomyopathy; alcoholic cardiomyopathy; supraventricular tachycardia; bradycardia; atrial flutter; hydrops fetalis; extrasystolic arrhythmia; fetal cardiac arrhythmia; endocarditis; atrial fibrillation; idiopathic dilated cardiomyopathy; Chagas' heart disease; long QT syndrome; and Brugada syndrome.

By "altered susceptibility" is intended that a transgenic animal of the invention differs from a non-transgenic animal in the extent to which the transgenic animal of the invention exhibits a cardiopathic phenotype. The cardiopathic phenotype may present during any stage of development including, but not limited to, embryonically, post-natally, in the adult, and as the animal nears end of lifespan. In an embodiment, the cardiopathic phenotype may be induced by external stimuli such as, but not limited to, diet, exercise, chemical treatment, or surgical procedure.

Cardiopathic phenotypes include, but are not limited to, hypertrophy; morphology, such as interventricular septal hypertrophy; left ventricular-end systolic $dP/dt_{max}$ or end-diastolic dimension(τ); papillary muscle dimension; left-ventricular outflow tract obstruction; midventricular hypertrophy; apical hypertrophy; asymmetrical hypertrophy; sarcomere structure; myofibril function; receptor expression; heart rate; ventricular systolic pressure; ventricular diastolic pressure; aortic systolic pressure; aortic diastolic pressure; contractility; interstitial fibrosis; cardiomyocyte disarray; $Ca^{2+}$ sensitivity; catecholine sensitivity; α-adrenergic sensitivity; beta-adrenergic sensitivity; dobutamine sensitivity; thyroxine sensitivity; angiotensin-converting enzyme inhibitor sensitivity; amiodarone sensitivity; lidocaine sensitivity; glycoprotein receptor antagonist sensitivity; anabolic steroid sensitivity; carnitine transport irregularities; left ventricular dilation, reduced left ventricular ejection fraction; left atrial dilatation; diuretic sensitivity; volemia; ischemia; leukocyte flow properties; the polymorphonuclear leukocyte (PMN) membrane fluidity; PMN cytosolic $Ca^{2+}$ content; high interventricular septal defects, rosette inhibition effect; contractile force transmission; myocardial fiber disarray, increased chamber stiffness, impaired relaxation, small-vessel disease, dyspnea, angina, presyncope, tachycardia, and syncope, and the like. See, for example, Braunwald et al. (2002) Circulation 106:1312–1316 and Wigle et al. (1995) Circulation 92:1680–1692, hereby incorporated by reference in their entirety.

Methods for measuring cardiopathic phenotypes are known in the art and include, but are not limited to, echocardiography, transesophageal echocardiography, exercise tests, urine/catecholamine analysis, EIAs, light microscopy, heart catheterization, dynamic electrocardiography, MRI, multiplex RT-PCR, positron emission tomography, angiography, magnetic resonance spin echo, short-axis MRI scanning, Doppler velocity recordings, Doppler color flow imaging, stress thallium studies, cardiac ultrasound, chest X-ray, oxygen consumption test, electrophysiological studies, auscultation, scanning EM, gravimetric analysis, H & E staining, skinned fiber analysis, transmission electron microscopy, immunofluorescent analysis, trichrome staining, 2-D echocardiography, cardiotocography, baseline M-mode echocardiography, and myocardial lactate production assays. See, for example, Braunwald et al. (2002) Circulation 106:1312–1316; Sohal et al. (2001) Circulation Res. 89:20–25; Nagueh et al. (2000) Circulation 102:1346–1350; Sanbe et al. (2001) J. Biol. Chem. 276: 32682–32686; Sanbe et al. (1999) J. Biol. Chem. 274: 21085–21094, and Wigle et al. (1995) Circulation 92:1680–1692, hereby incorporated by reference in their entirety.

In an embodiment, a transgenic animal of the invention may be used to identify anti-cardiopathic compounds. An "anticardiopathic" compound modulates a cardiopathic phenotype. Modulation may be an increase or decrease in a cardiopathic phenotype. An anticardiopathic compound will modulate a cardiopathic phenotype by at least 1%, 5%, preferably 10%, 20%, more preferably 30%, 40%, 50%, 60%, yet more preferably 70%, 80%, 90%, or 100% as compared to an untreated or placebo treatment effect. Methods for assaying cardiopathic phenotypes are described elsewhere herein. Any method of assaying a cardiopathic phenotype known in the art may be used to monitor the effects of the compound of interest on a transgenic animal of the invention.

To identify anti-cardiopathic compounds, multiple transgenic animals of the invention, e.g. at least a first and second transgenic animal, are provided. The terms "first," "experimental," or "test" transgenic animal refer to a transgenic animal to which a compound of interest is administered. The terms "second" or "control" transgenic animal refer to a transgenic animal to which a placebo is administered. In an embodiment, the first and second transgenic animals are clonal, age-matched, gender-matched, and subject to similar environmental conditions. In an embodiment, more than one animal may be a first transgenic animal. In an embodiment more than one animal may be a second transgenic animal.

After administration of either the compound of interest or the placebo, the first and second transgenic animals are incubated for a period of time. The period of time will have a predetermined duration appropriate to analysis of the cardiopathic phenotype. Such durations include, but are not limited to, 30 seconds; 1, 5, 10, 30, or 60 minutes; 8, 12, 24, 36, or 48 hours; 3, 4, 5, 6, or 7 days; 2, 3, or 4 weeks; 2, 3, 4, 5, 6, 7, 8, 9, 10, 11, or 12 months; up to 3 years. Monitoring of a cardiopathic phenotype may occur continuously; at a single interval; or at multiple intervals, such as, but not limited to, hourly, daily, weekly, and monthly. Any method of assaying a cardiopathic phenotype known in the art may be used to monitor the effects of the compound of interest on a transgenic animal of the invention.

The term "administer" is used in its broadest sense and includes any method of introducing a compound into a transgenic animal of the present invention. This includes producing polypeptides or polynucleotides in vivo as by transcription or translation in vivo of polynucleotides that have been exogenously introduced into a subject. Thus, polypeptides or nucleic acids produced in the subject from the exogenous compositions are encompassed in the term "administer."

A "compound" comprises, but is not limited to, nucleic acid molecules, peptides, peptidomimetics, lipids, antibodies, receptor inhibitors, ligands, sterols, steroids, hormones, kinases, kinase inhibitors, agonists, antagonists, ion-channel modulators, diuretics, enzymes, enzyme inhibitors, carbohydrates, deaminases, deaminase inhibitors, G-proteins, G-protein receptor inhibitors, ACE inhibitors, hormone receptor modulators, alcohols, reverse transcriptase inhibitors, neurotransmitter inhibitors, angiotensin converting enzyme inhibitors, digitalis, neurotransmitter receptor modulators, negative inotropic agents, β-blockers, $Ca^{2+}$ antagonists, disopyramide, anti-arrhythmia agents, hormones, flecainide, and vasodilators. A compound may additionally comprise a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a carboxypeptidase protein or anti-carboxypeptidase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Anti-cardiopathic compounds identified by the methods of this invention may be used in the treatment of human individuals.

The following examples are offered by way of illustration and not by way of limitation.

EXPERIMENTAL

EXAMPLE 1

Generation of the Inducible Cardiac-Preferred Promoter of the Invention

The modified alpha promoter described in *Transgenic Research* (1995) 4:397–405, herein incorporated by reference was used as the starting point for making the minimal promoter of the invention. All restriction endonucleases were from Roche BioPharmeceuticals, Indianapolis, Ind. Restriction enzyme reactions were performed according to standard protocols. Two fragments were excised from the modified alpha promoter.

A ~700 bp Sma1-Sph1 fragment was modified by PCR. A TTGA sequence replaced the TATC sequence starting at approximately position 2456. The approximately 1.7 kb Sph1-Nde1 segment was modified. The sequence TGCAT-GCCCTGA (SEQ ID NO:2) replaced the sequence TATCT-GCCCATC (SEQ ID NO:3). The insertion of SEQ ID NO:3 introduced an additional Sph1 restriction enzyme site and altered 2 GATA sites near position 4106. An approximately 300 base pair fragment comprising SEQ ID NO:4 repeated seven times was inserted into the Sph1-Nde1 segment near position 4282. The seven repeat binding site was inserted beginning at position 4282. The repeat consisted of the sequence TCGAGTTTACCACTCCCTATCAGTGATA-GAGAAAAGTGAAAG (SEQ ID NO:4).

The smaller fragments were ligated together before being put back into the full length promoter. First the Sma1-Sph1 fragment was cut with Sph1 and Nde1 and the 510 bp Nde1-Sph1 fragment was ligated to the vector. The resulting clone was opened with Sph1 and the ~1460 bp Sph1 fragment obtained from Sph1 digestion of the modified Sph1-Nde1 segment was added. The orientation was checked by PCR. The clone was next digested with Sma1 and Nde1. The Sma1-Nde1 fragment replaced the wild type sequences in the original alpha promoter. The wild type sequences were removed by doing a complete Nde digest along with a partial Sma digest. The complete MHCmin$^{TetO}$ inducible, cardiac-preferred promoter sequence was sequenced so as to confirm the modified bases and is set forth in SEQ ID NO:1.

EXAMPLE 2

Generation of ELC1a Expression Cassette

A plasmid containing the MHCmin$^{teto}$-inducible promoter region (SEQ ID NO:1) was digested with the restriction enzyme, Sal I and linearized. A 9142 base pair fragment was purified from agarose. The mouse ELC1a cDNA (Fewell, et al. (1998) *J Clin Invest.* 101:2630–2639, herein incorporated by reference in its entirety) was digested with Sal I and a 627 base pair cDNA fragment coding a ELC1a gene (SEQ ID NO:5) was purified from agarose. The ELC1a fragment was ligated into the MHCmin$^{teto}$-inducible promoter region with the rapid ligation kit (Roche, Indianapolis, Ind.). The plasmid containing ELC1a linked to a MHCmin$^{teto}$ inducible promoter was digested with Not I. The final 9769 base pair fragment was purified from agarose and used for injection.

EXAMPLE 3

Generation of GSK-3β CA Expression Cassette

A full-length murine glycogen synthase kinase 3β (GSK-3β) cDNA (Genbank BC00693) was synthesized using reverse transcription (RT)-PCR with poly A+RNA isolated from an Fvb/N mouse ventricle as a template. Primers with Sal I site at the termini were made to the 3' and 5' untranslated region of GSK3β cDNA. The 5' primer was GTCGA-CAAGAAGAG CCATCATGTCGGGGCGAC (SEQ ID NO:9) and the 3' end was GTCGACTGTTCAAGCG-TAGTCTGGGACGTCGTATGGGTAGGTG-GAGTTGGAA GCTGATGCAG (SEQ ID NO:10). The 3' end primer contained a haemagglutinin epitope tag sequence to introduce this tag sequence into the GSK-3β cDNA. To make the constitutive active form of the GSK-3β, the serine at position 9 of the amino acid coding region was mutated to alanine by PCR (TCC→GCG). The mutated GSK-3β (S9A) was ligated into a plasmid vector and sequenced. The plasmid containing the GSK3-β S9A (GSK-3β CA; SEQ ID NO:7) was digested with Sal I. A 1318 base pair fragment of the GSK-3β CA was purified and ligated into the fragment of MHCmin$^{teto}$-inducible promoter cassette, which was digested with Sal I and purified from agarose. The final 10460 base pair fragment was purified from agarose and used for injection.

EXAMPLE 4

Generation of Transgenic Mice

The expression cassettes described herein above were digested free of vector sequences with NotI and purified from agarose. The expression cassettes were prepared for microinjection as described in Hogan, et al. 1986 *Manipulating the Mouse Embryo: A Laboratory Manual*, Cold Spring Harbor, N.Y., Cold Spring Harbor Laboratory pp89–197, herein incorporated by reference in its entirety. Single cell embryos derived from superovulated FVB/N females were used in the microinjections. Surviving microinjected embryos were implanted into pseudopregnant CBA/B6 foster mothers. Founder mice were identified by the polymerase chain reaction and confirmed by genomic Southern blots using DNA obtained from tail clips. Stable transgenic lines were generated by breeding the founder mice with nontransgenic littermates. Subsequent offspring were screened by PCR. Stable transgenic lines were screened for inducible expression patterns (FIG. 1, Panel A, described elsewhere herein). Multiple tissues from transgenic mice were screened for expression (FIG. 1, Panel B).

Stable transgenic lines exhibiting the desired expression pattern were bred with transgenic lines carrying the original tetracycline-controlled transcriptional activator construct (Gossen, et al. (1994) *Curr. Opin. Biotechnol.* 5:516–520, herein incorporated by reference in its entirety) operably linked to the murine α-MHC promoter at the SalI restriction enzyme site.

The double transgenic line was breed to homozygosity at the MHCmin$^{TetO}$-ELC1a locus.

EXAMPLE 5

Detection of ELC1a Expression

ELC1a expression from the promoter of the invention was detected by several methods. Mice from a non-transgenic line and three transgenic lines were euthanized by $CO_2$ asphyxiation. The three transgenic lines contained the MHCmin$^{TetO}$-ELC1a expression cassette. Atrial and left ventricular tissues were freshly isolated from a non-transgenic mouse line. Left and right ventricular tissues were freshly isolated from three transgenic mouse lines.

ELC1a expression was analyzed by RNA dot blots. Tissue samples were homogenized in Tri-Reagent (Molecular Research Center, Cincinnati Ohio). Total RNA was extracted according to the manufacturer's instructions. 5 μg RNA from each tissue was blotted onto nitrocellulose and hybridized to an ELC1a specific oligonucleotide probe. The data was normalized using GAPDH (glyceraldehyde 3-phosphate dehydrogenase) expression. Hybridization signals were collected on a Phosphorimager (Molecular Dynamics). Results obtained are presented in FIG. 1A.

ELC1a expression was also analyzed by Western blot analysis. Myofibrillar proteins were isolated by the methods known to one skilled in the art (Sanbe et al. (1999). *J. Biol. Chem.* 274:21085–21094 and McAuliffe et al. (1990) *Circ. Res.* 66:1204–1216, herein incorporated by reference in their entirety.). Protein samples were loaded on an SDS-polyacrylamide gel and electrophoresed at 120 Volts for approximately 3 hours. The proteins were transferred from the SDS-PA gels onto PVDF membranes (Amersham Life Sciences, Buckinghamshire, England) at 4° C. overnight. The membranes were probed with rabbit polyclonal antisera against ELC1a (Genemed Biotech, California). Results obtained are presented in FIG. 1B.

ELC1a expression in numerous tissues was analyzed by Western blot. Atrial tissue was isolated from a non-transgenic mouse. Left ventricular, right ventricular, atrial, diaphragm, soleus, bicep, tibialis, masseter, tongue, stomach, small intestine, aorta, lung, liver, and spleen tissues were dissected from a transgenic mouse carrying the ELC1a expression cassette. Western blots were performed as described above. Results obtained are presented in FIG. 1C.

EXAMPLE 6

Effect of Doxycycline on ELC1a Expression

Figure 2:
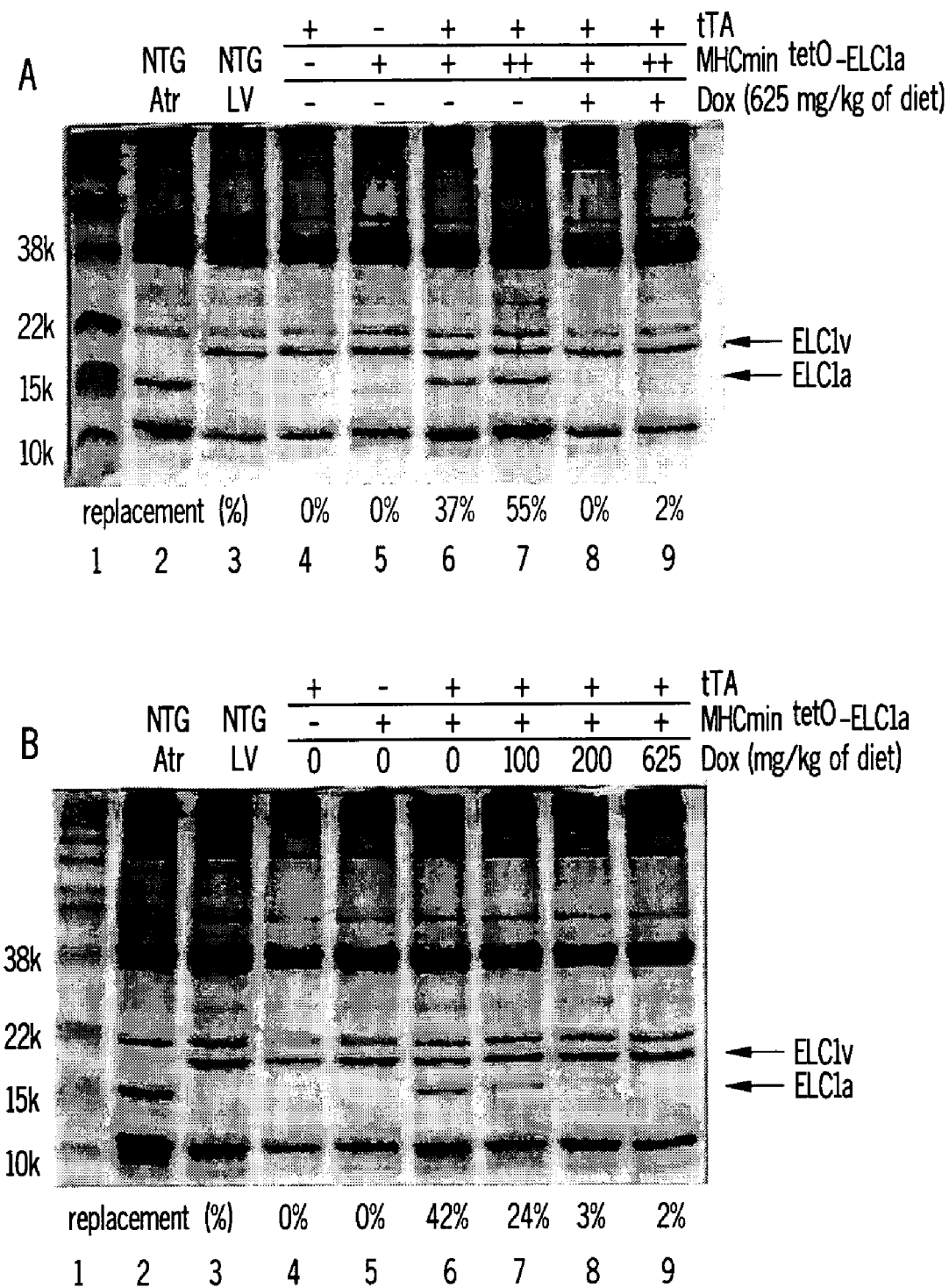
FIG. 2 presents the results of polyacrylamide gel electrophoresis of myofilament proteins. The gels were stained with Coomassie. The migration pattern of the ventricular (ELC1v) and atrial (ELC1a) isoforms is indicated with arrows on the right of the gels. The percent to which the transgenic atrial isoform replaced the native ELC1v isoform is indicated below each lane. Panel A presents the results from several mouse lines in the presence or absence of doxycycline (625 mg/kg chow). Lane 1 contains molecular weight markers, with the sizes indicated to the left of the gel. Lanes 2 and 3 contain proteins isolated from atrial and left ventricular tissue of a non-transgenic control, respectively. Lanes 4–9 contain proteins isolated from ventricular tissue of several transgenic lines. The transgenic line represented in Lane 4 contains the activator construct (tTA). The transgenic line represented in Lane 5 contains the responder construct of the invention operably linked to the ELC1a gene (MHCmin$^{TetO}$-ELC1a). The double transgenic line represented in Lane 6 contains both the activator construct (tTA) and the responder construct operably linked to the ELC1a gene (MHCmin$^{TetO}$-ELC1a;). Protein from an MHCmin$^{TetO}$-ELC1a homozygous transgenic line was loaded in lane 7. Lanes 8 and 9 contain protein from animals fed doxycycline (Dox) (625 mg/kg of diet). The double transgenic line is represented in Lane 8. Lane 9 contains protein from the MHCmin$^{TetO}$-ELC1a homozygous transgenic line.

Non-transgenic mice and mice from numerous transgenic lines were raised according to routine laboratory animal handling practice. The transgenic lines were the tTA activator single transgene line, the MHCmin$^{TetO}$-ELC1a single transgene line, the double tTA activator/MHCmin$^{TetO}$-ELC1a responder line, and the double tTA activator/MHCmin$^{TetO}$-ELC1a homozygous responder line. Three weeks prior to harvest, the diets of the heterozygous and homozygous MHCmin$^{TetO}$-ELC1a double transgenic mice were supplemented with 625 mg doxycycline/kg feed. Atrial and left ventricular proteins were obtained from a non-transgenic mouse. Myofilament proteins were obtained from the two single transgenic lines, the MHCmin$^{TetO}$-ELC1a heterozygous and homozygous double transgenic lines, and the doxycycline fed MHCmin$^{TetO}$-ELC1a heterozygous and homozygous double transgenic lines. The proteins were loaded on SDS/Polyacrylamide gels. The gels were electrophoresed as described herein. The gels were stained with Coomassie stain. The percent of ELC1-v replaced by the transgenic ELC1-a was determined by electrophoretic analysis and quantification using NIH Image software on a MacIntosh G4 computer. Results obtained from one such experiment are presented in FIG. 2, Panel A.

EXAMPLE 7

Effect of Doxycycline Level on ELC1a Expression

Mice from the tTA activator single transgenic line, the MHCmin$^{TetO}$-ELC1a single transgenic line, and the MHCmin$^{TetO}$-ELC1a heterozygous and homozygous double transgenic lines were raised according to routine laboratory animal handling practices. The diets of heterozygous MHCmin$^{TetO}$-ELC1a double transgenic mice were supplemented with 0, 100, 200, or 625 mg doxycycline/kg feed beginning three weeks prior to harvest.

Atrial and left ventricular proteins were obtained from a non-transgenic mouse. Myofilament proteins were obtained from the two single transgenic lines, the MHCmin$^{TetO}$-ELC1a heterozygous and homozygous double transgenic lines, and the doxycycline fed MHCmin$^{TetO}$-ELC1a heterozygous and homozygous double transgenic lines. The proteins were loaded on SDS/Polyacrylamide gels. The gels were electrophoresed as described herein. The gels were stained with Coomassie stain. The percent of ELC1-v replaced by the transgenic ELC1a was determined by by electrophoretic analysis and quantification using NIH Image software on a MacIntosh G4 computer. Results obtained from one such experiment are presented in FIG. 2, Panel B.

EXAMPLE 8

Detection of GSK-CA Expression in Ventricular Tissue of Transgenic Mice

As described in Example 3, a nucleotide sequence encoding a constitutively active form of the serine/threonine kinase GSK-3β was cloned into an expression cassette comprising the MHCmin$^{TetO}$ promoter of the invention using standard molecular biology techniques. The MHCmin$^{TetO}$-GSK-CA expression cassette was used to generate transgenic mice as described in Example 4. As described elsewhere herein (see Example 4), the MHCmin$^{TetO}$-GSK-CA single transgenic mice were bred with tTA activator single transgenic mice to yield double transgenic mice.

Male, age-matched nontransgenic mice and six double transgenic mice were maintained on a doxycycline-free or doxycycline-containing diet for 6 weeks. At 6 weeks doxycycline was withdrawn from the diets of three of the double transgenic mice. At seven weeks, myofibrillar proteins were harvested from the eight animals as described elsewhere herein. The proteins were loaded on SDS-polyacrylamide gels and electrophoresed as described elsewhere herein. The proteins were transferred to PVDF membranes at 4° C. overnight. The membranes were probed with either anti-GSK-3β (BD Transduction Laboratory, NJ) or anti-HA antisera (Santa Cruz Biotechnology, CA). Results obtained from one such experiment are presented in FIG. 3, Panel D.

EXAMPLE 9

Assessment of the Murine Hypertrophic Response

Two cohorts of age-matched, male non-transgenic mice were established. Transaortic coarctation (TAC) procedures were performed on one cohort while sham operations were performed on the second cohort. TAC and sham TAC procedures are known to one skilled in the art (Dorn et al. (1994) *Am. J. Physiol.* 267:H400–5, herein incorporated by reference). Mice from the TAC and sham cohorts were analyzed at the time of the procedure and 1, 2, 3, 4, 5, 6, and 7 weeks after the operation.

The total body mass of each mouse analyzed at a time point was determined. Mice were $CO_2$ euthanized and the left ventricles were removed. The left ventricle mass was determined. The ratio of the left ventricle mass to the total body mass was determined at each time point. Results obtained from one such experiment are presented in FIG. 3, Panel B.

EXAMPLE 10

Determination of Effect of GSK-CA on the Hypertrophic Response

Nine cohorts of 4–6 male, 12 week old mice were established. Sham TAC procedures were performed on non-transgenic mice, tTA activator single transgenic mice, MHCmin$^{TetO}$-GSK-CA single transgenic mice, and tTA activator/MHCmin$^{TetO}$-GSK-CA double transgenic mice. TAC procedures were performed on mice from a non-transgenic and double transgenic cohort. Two weeks after the procedures, the experiment was terminated. After termination, left ventricle/total body mass ratios were determined.

A separate protocol (Protocol 2) was performed on three cohorts: a non-transgenic cohort and two cohorts of double transgenic mice. The diet of the double transgenic mice was supplemented with doxycycline at 625 mg/kg feed for 4 weeks prior to the TAC procedure. The TAC procedure was performed on the three cohorts. Doxycycline was maintained in the diet of one double transgenic cohort. One week after the TAC procedure, doxycycline was withdrawn from the diet of the second double transgenic cohort. The experiment was terminated seven weeks after the TAC operations. Left ventricle/total body mass ratios were determined for the 3 cohorts.

Figure 3:
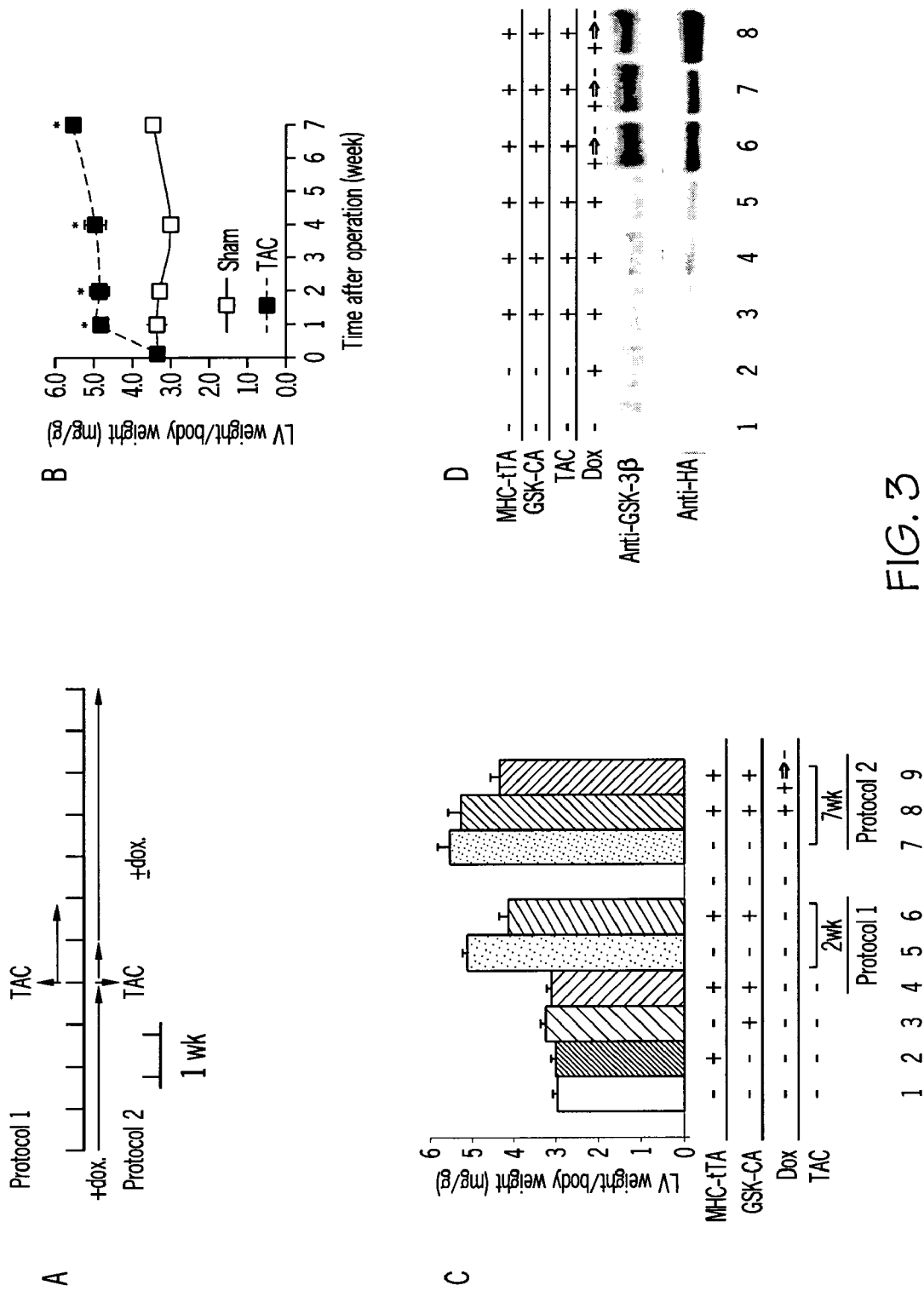
FIG. 3 depicts the results of analysis of the regulation of the hypertrophic response in animals expressing active GSK-3β. Experimental details are described elsewhere herein. A nucleic acid molecule encoding a constitutively active form of GSK-3β with a haemagglutinin epitope at the C-terminus was operably linked to the promoter of the invention.

Results from one such experiment are presented in FIG. 3, Panel C.

EXAMPLE 11

Method of Identifying Anti-Cardiopathic Compounds

This assay can be used for a variety of cardiopathic phenotypes. A nucleotide sequence of interest is cloned into an expression vector containing a promoter of the invention. The expression cassette comprising the promoter of the invention, MHCmin$^{TetO}$, operably linked to the nucleotide sequence of interest is digested with a restriction enzyme. The restriction reaction products are electrophoresed on an agarose gel, and the expression cassette is purified from the agarose. The expression cassette is prepared for microinjection according to any method known to one skilled in the art. The expression cassette is used to provide a transgenic mouse. The presence of the transgene is confirmed using Southern blot analysis. Single transgenic mice are mated to transgenic mice containing the tTA activator transgene to yield double transgenic mice comprising the tTA activator transgene and the promoter of the invention operably linked to the nucleotide sequence of interest.

Two cohorts of age-matched double transgenic mice are established. Doxycycline is used to regulate expression of the nucleotide sequence of interest. The diet of one cohort is supplemented with a compound of interest. The diet of the second cohort is supplemented with a placebo. The two mice cohorts are incubated for an appropriate time and the experiment is terminated. The mice are monitored for a cardiopathic phenotype such as hypertrophy using the left ventricle/body mass ratios described elsewhere herein. The cardiopathic phenotype presented by the mice of the each cohort is compared.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule having the nucleotide sequence comprising the sequence set forth in SEQ ID NO:1.

2. An expression cassette comprising the isolated nucleic acid molecule of claim 1 operably linked to a nucleotide sequence of interest.

3. A vector comprising the expression cassette of claim 2.

4. An isolated host cell stably transformed with the expression cassette of claim 2.

5. The isolated host cell of claim 4, wherein said host cell is an animal cell.

6. The isolated nucleic acid molecule of claim 1, wherein said nucleotide sequence is capable of initiating cardiac-preferred transcription.

7. The isolated nucleic acid molecule of claim 6, wherein said cardiac-preferred transcription is ventricle-preferred.

8. The isolated nucleic acid molecule of claim 6, wherein said cardiac-preferred transcription is inducible.

* * * * *